US010576233B2

(12) United States Patent
Harwood et al.

(10) Patent No.: US 10,576,233 B2
(45) Date of Patent: Mar. 3, 2020

(54) NASAL INTERFACES FOR RESPIRATORY THERAPY

(71) Applicant: Fisher & Paykel Healthcare Limited, Auckland (NZ)

(72) Inventors: Jonathan David Harwood, Auckland (NZ); Andrew Paul Maxwell Salmon, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 817 days.

(21) Appl. No.: 14/424,331

(22) PCT Filed: Aug. 29, 2013

(86) PCT No.: PCT/NZ2013/000152
§ 371 (c)(1),
(2) Date: Feb. 26, 2015

(87) PCT Pub. No.: WO2014/035261
PCT Pub. Date: Mar. 6, 2014

(65) Prior Publication Data
US 2015/0209541 A1    Jul. 30, 2015

Related U.S. Application Data

(60) Provisional application No. 61/694,707, filed on Aug. 29, 2012.

(51) Int. Cl.
*A61M 16/06* (2006.01)
*A61M 16/08* (2006.01)

(52) U.S. Cl.
CPC .... *A61M 16/0666* (2013.01); *A61M 16/0622* (2014.02); *A61M 16/0683* (2013.01); *A61M 16/0816* (2013.01); *A61M 2205/42* (2013.01)

(58) Field of Classification Search
CPC ........ A61M 16/00; A61M 16/06–0694; A61M 16/20–209; A61M 16/0003–0012;
(Continued)

(56) References Cited

U.S. PATENT DOCUMENTS 5,429,683 A * 7/1995 Le Mitouard ......... A61M 16/06
128/205.25
5,662,101 A * 9/1997 Ogden .................. A61M 16/06
128/202.27
(Continued)

FOREIGN PATENT DOCUMENTS

WO    WO 2011/110961 A1    9/2011

OTHER PUBLICATIONS

International Search Report; PCT/NZ2013/000152; dated Jan. 30, 2014.
Written Opinion, PCT/NZ2013/000152, dated Jan. 30, 2014.

*Primary Examiner* — Tan-Uyen T Ho
*Assistant Examiner* — Ned T Heffner
(74) *Attorney, Agent, or Firm* — Knobbe, Martens, Olson & Bear, LLP

(57) ABSTRACT

Patient interfaces for respiratory therapy in the form of nasal interfaces or nasal masks include features that enhance or provide lateral stability of the interface. At least some of the embodiments provide multiple facial contact points or areas located in the general areas of the user's cheeks and/or upper lip. Some embodiments of the nasal interfaces provide advantageous sealing characteristics. The nasal interfaces may provide a controlled expiratory flow to reduce noise. Some embodiments include nasal pillows instead of or in addition to nasal prongs. The nasal pillows can have exhaust vents or can change in length in response to a pressure level within the nasal pillow.

22 Claims, 40 Drawing Sheets

(58) Field of Classification Search
CPC . A61M 2016/0015–0042; B63C 11/12; B63C 11/18; A62B 18/00; A62B 18/10; A62B 7/00; A62B 7/04; A62B 7/14; A62B 9/00; A62B 9/02–027
See application file for complete search history.

(56) References Cited

U.S. PATENT DOCUMENTS

| | | |
|---|---|---|
| 5,724,965 A | 3/1998 | Handke et al. |
| 6,119,694 A | 9/2000 | Correa et al. |
| 2004/0025883 A1* | 2/2004 | Eaton ............... A61M 16/0683 128/206.27 |
| 2006/0283461 A1* | 12/2006 | Lubke .................. A61M 16/06 128/207.11 |
| 2007/0209663 A1 | 9/2007 | Marque et al. |
| 2011/0146685 A1* | 6/2011 | Allan .................. A61M 16/06 128/205.25 |

\* cited by examiner

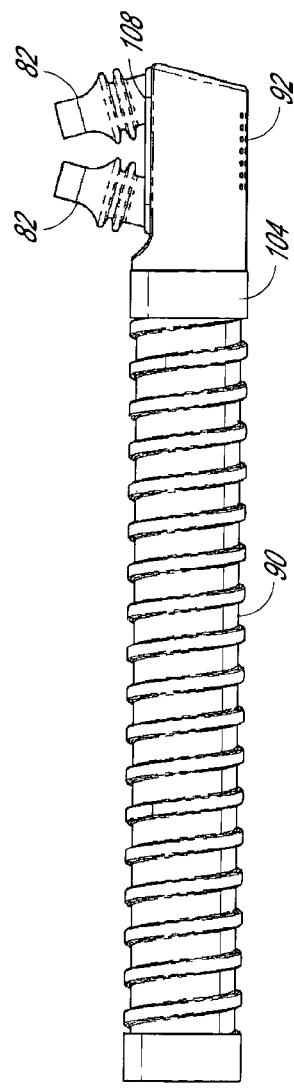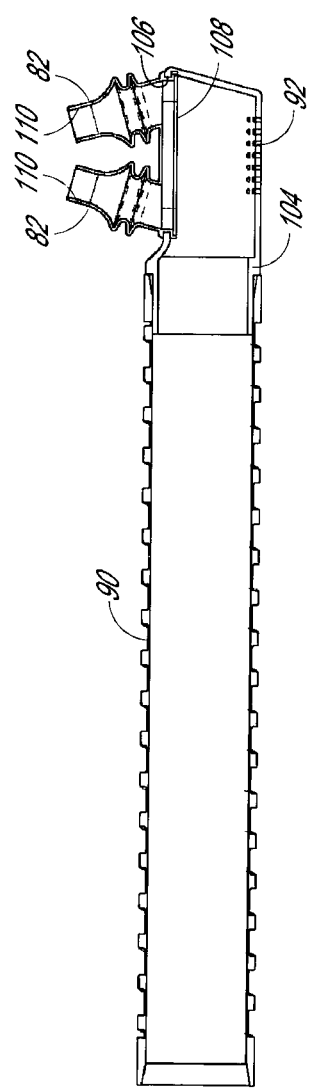

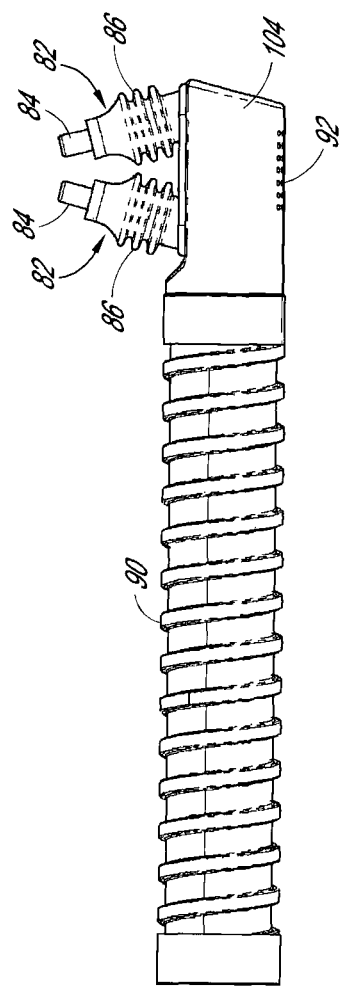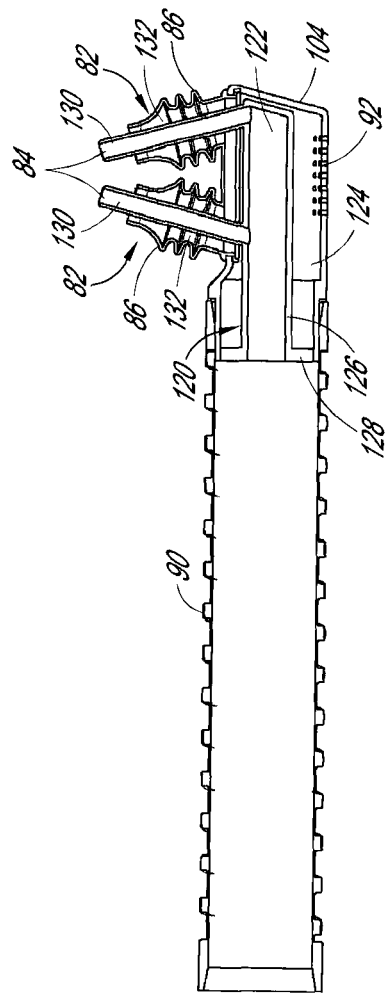

NASAL INTERFACES FOR RESPIRATORY THERAPY

BACKGROUND OF THE INVENTION

Field of the Invention

The present invention generally relates to patient interfaces for use in respiratory therapy, including but not limited to CPAP and nasal high flow therapies (HFT). More particularly, the present invention relates to nasal interfaces.

Description of the Related Art

Nasal interfaces, such as nasal masks, are sometimes utilized as a patient interface in various forms of respiratory therapy. Nasal masks often utilize a set of nasal prongs, which are inserted into the nares of the user, a face mask, which support the nasal prongs, and a strap or harness to hold the frame in place on the user's head. In some forms of respiratory therapy, nasal masks can alternatively utilize a set of nasal pillows, which sit under the nares. The nasal pillows form a seal with the outer perimeter of the user's nares and often protrude a distance into the nares. These configurations often also include a frame that supports the pillows and headgear, which holds the mask on the user's head.

SUMMARY OF THE INVENTION

A need exists for improved or alternative nasal interfaces or masks. In particular, because nasal masks are often used for significant periods of time, features that provide improved comfort to the user relative to traditional cannula designs are desirable. In addition, it is often desirable to maintain an adequate seal despite small or subtle movements of the nasal mask on the user's face. Thus, a need exists for a nasal mask having features that improve the stability of the mask on the user's face. Traditional cannula designs using unsealed nasal prongs can generate significant noise, especially in the context of HFT. Accordingly, arrangements that provide noise reduction relative to traditional cannula designs are desirable. Preferably, the disclosed nasal masks address one or more of these design criteria.

The systems, methods and devices described herein have innovative aspects, no single one of which is indispensable or solely responsible for their desirable attributes. Without limiting the scope of the claims, some of the advantageous features will now be summarized.

An embodiment involves a nasal interface for delivering respiratory therapy to a user, including a frame, at least one nasal delivery element supported by the frame and that delivers a flow of breathing gas to the nares of the user, a conduit that delivers the flow of breathing gas to the at least one nasal delivery element, a headgear that secures the frame to the head of the user and at least two lateral supports located on a face of the user on opposite lateral sides of the user's nose supporting the frame relative to the user's nose.

In some configurations, a retention force of the headgear is translated to the frame and then to the face of the user through the at least two lateral supports. In some configurations, a retention force of the headgear is translated to the at least two lateral supports and then to the face of the user with the frame positioning the at least two lateral supports relative to one another.

In some configurations, the at least one nasal element is a pair of prongs. In some configurations, the at least one nasal element is a pair of nasal pillows. In some such configurations, a sealing force applied by the nasal pillows to the nares is predominantly a function of the longitudinal rigidity of the nasal pillows. In some configurations, the longitudinal rigidity of the nasal pillows changes with the delivery pressure of the breathing gas. The longitudinal rigidity of the nasal pillows can increase as the delivery pressure increases.

In some configurations, the at least one nasal delivery element is a nasal seal. The at least one nasal delivery element can be a pair of nasal delivery elements, each comprising an inner nasal prong and an outer nasal pillow.

In some configurations, the frame is connected to at least one additional support located on the face of the user below the nose. In some configurations, each of the at least two lateral supports are located on or near the junction of the zygomatic bone and the maxilla. At least one additional support can be located on the maxilla. The at least one additional support can comprise a pair of supports located on either side of the user's nose.

In some configurations, at least a portion of the frame is formable to permit customization to the user. At least a central portion of the frame can be spaced away from contact with the user's face. The lateral supports can be defined by portions of the headgear or are carried by the headgear. The frame can extend between first and second portions of the headgear and can be supported away from user's face by the headgear. The headgear can include a front portion that extends rearwardly from each of the user's cheeks and a top portion that extends over the crown of the user's head, wherein one or both of the front portion and the top portion is constructed from a rigid or semi-rigid material.

In some configurations, first and second lateral arms carry or define a respective one of the lateral supports. The first and second lateral arms can be supported by the frame. The first and second lateral arms can be supported by the headgear. In some configurations, the first and second lateral arms are formable. The length of the first and second lateral arms can be adjustable. A portion of each of the first and second lateral arms can be covered with a soft sleeve. In some configurations, the first and second lateral arms are positioned such that the first and second lateral contact surfaces are located on the inner cheeks adjacent the user's nose. A position of the pair of lateral supports can be adjustable.

In some configurations, a pair of stabilizing portions are positioned to contact opposite sides of the user's nose to assist in stabilizing the nasal interface in a lateral direction on the user's face. The pair of stabilizing portions can be defined by a pair of cushions supported by the frame. In some configurations, the stabilizing portions are extensions of the at least one additional support.

In some configurations, the frame includes embedded or external formable members. The frame can include a pair of hinged members pivotally coupled to a main portion of the frame, each of the pair of hinged members carrying or defining a respective one of the lateral supports.

In some configurations, the nasal interface includes a manifold that supports the pair of nasal delivery elements. The pair of nasal delivery elements can be carried by an insert that is removable from the manifold. The manifold can be removable from the frame and can be inserted into the frame in either of two orientations such that the conduit can be directed in a desired one of two orientations. The manifold can be rotatable relative to the frame to adjust an angular orientation of the nasal delivery elements. The nasal interface can include a bias flow outlet in one of the frame or the manifold and an opening in the other of the frame or the manifold that is aligned with the bias flow outlet.

In some configurations, an elbow connects the conduit to the frame. The elbow can be adjustable relative to the frame about at least one axis. The elbow can define a bias flow outlet.

In some configurations, a nasal interface for delivering respiratory therapy to a user includes a frame, a pair of nasal delivery elements supported by the frame and that delivers a flow of breathing gas to the nares of the user, a conduit that delivers the flow of breathing gas to the pair of nasal delivery elements, a headgear that secures the frame to the head of the user, and at least one lip support defining a lip contact surface that contacts an upper lip of the user, wherein the at least one lip support spaces at least a central portion of the frame away from the face of the user.

In some configurations, the lip contact surface has opposing lateral edges that are located at or near the corners of the user's mouth. In some configurations, the at least one lip support comprises a first lip support defining a first lip contact surface and a second lip support defining a second lip contact surface that is discrete from the first lip contact surface.

In some configurations, a nasal interface for delivering respiratory therapy to a user includes a frame, a pair of nasal pillows supported by the frame and that delivers a flow of breathing gas to the nares of the user, a conduit that delivers the flow of breathing gas to the pair of nasal delivery elements and a headgear that secures the frame to the head of the user. The nasal pillows include a base, a nare-contacting portion and a thin-walled portion between the base and the nare-contacting portion. Each of the nasal pillows extends longitudinally with pressure.

In some configurations, each of the nasal pillows includes a deformable support for supporting the nare-contacting portion at low pressure. The nasal pillows can include a thickened nare-contacting portion. The base can define a gas entry to the nasal pillow and the nare-contacting portion can define a gas exit from the nasal pillow. The gas entry can be larger than the gas exit to facilitate pressure build up within the nasal pillow.

In some configurations, a nasal interface for delivering respiratory therapy to a user includes a frame, a pair of nasal delivery elements supported by the frame and that deliver a flow of breathing gas to the nares of the user, a conduit that delivers the flow of breathing gas to the pair of nasal delivery elements and a headgear that secures the frame to the head of the user. Each of the pair of nasal delivery elements includes an inner prong that protrudes into the nare of the user and an outer nasal pillow that seals on the outer surfaces of the nare.

In some configurations, gas is delivered to the nare through the prong and gas exits the nare through a space between the prong and the nasal pillow. The nasal pillow can include a plurality of gas exhaust vents that direct gas away from the nare. The nasal interface can include a diffuser that cooperates with the gas exhaust vents to reduce draft or noise from the exhaust vents. The exhaust vents can be configured to regulate bias gas flow from the interface during the delivery of positive airway pressure treatment. In some configurations, the exhaust vents are configured to regulate positive expiratory pressure during the delivery of nasal high flow therapy.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 14 is a front view of a manifold and breathing tube of the nasal interface of FIG. 8 separated from a frame of the nasal interface.

FIG. 15 is a sectional view of the manifold and breathing tube of FIG. 14.

FIG. 17 is a front view of an embodiment of a manifold and breathing tube that can be used with nasal interfaces disclosed herein. The manifold and breathing tube define inspiration and expiration flow paths that are at least partially separate from one another.

FIG. 18 is a sectional view of the manifold and breathing tube of FIG. 17.

DETAILED DESCRIPTION OF THE PREFERRED EMBODIMENTS

Figure 1:
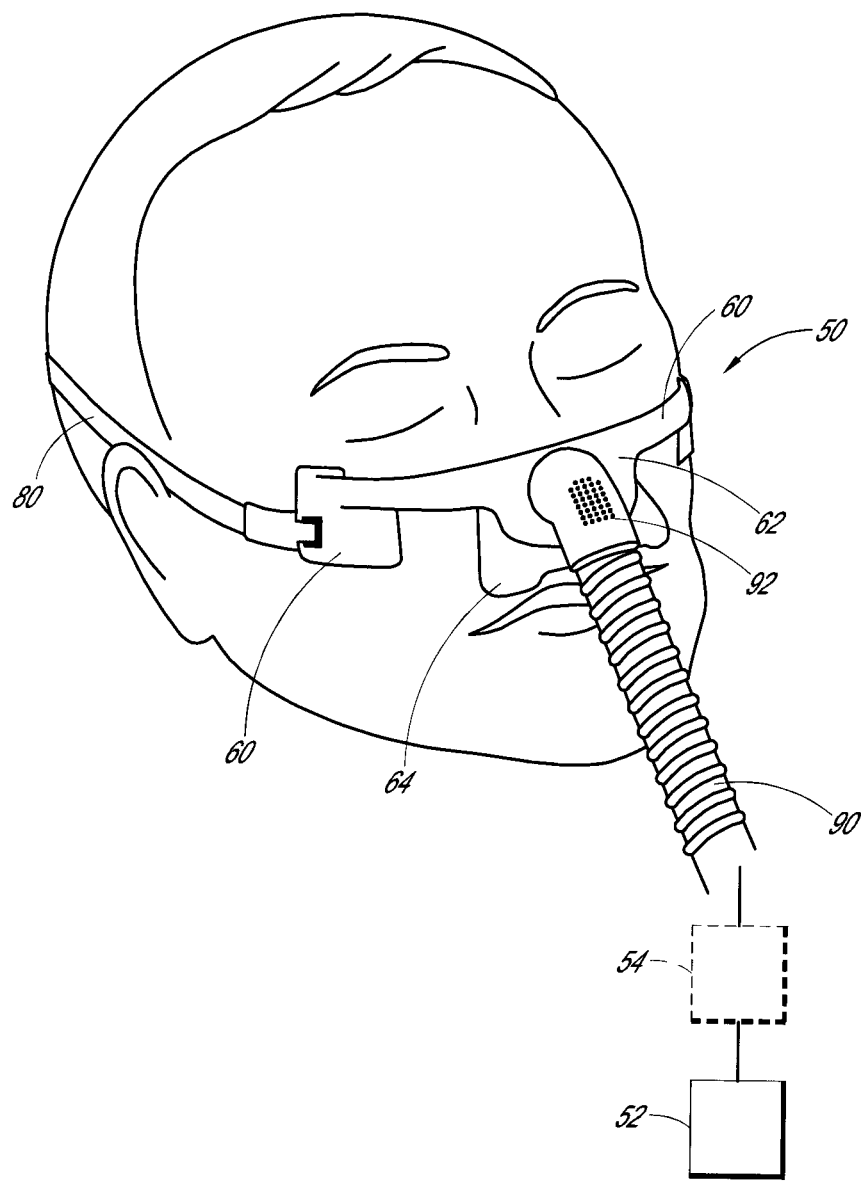
FIG. 1 is a front perspective view of an embodiment of a nasal interface positioned on a user.

FIGS. 1-47 illustrate preferred patient interfaces in the form of nasal interfaces or nasal masks that may be useful in various forms of respiratory therapy. Some embodiments include features that enhance or provide lateral stability of the interface to inhibit or prevent the cannula prongs or other nasal elements from being dislodged from the nares during movement. At least some of the embodiments provide multiple facial contact points or areas that aid the stability of the nasal interface on the user's face. These contact points or areas preferably are located in the general areas of the user's cheeks and/or upper lip. In embodiments that provide only one or two contact points or areas, it can be preferable that the contacting structures have a surface area large enough to spread the load over a region of the user's cheeks or other portion of the face, rather than creating a point load which could be uncomfortable and/or unstable. Preferably, the embodiments of the patient interface disclosed herein create a stable platform for supporting nasal delivery element(s) (e.g., mask, prongs, pillows or a combination of any of these). Advantageously, such an arrangement permits a sealing force of the nasal delivery elements to be largely or substantially completely separated or decoupled from a retention force of the headgear. That is, the headgear can be adjusted or tightened to comfortably secure the frame to the user's face without significantly influencing the sealing force of the nasal delivery elements. Rather, the sealing force can be determined by frame and/or nasal delivery element design.

One or more of the illustrated nasal interfaces preferably provide advantageous sealing characteristics. Some embodiments provide a controlled expiratory flow to reduce or minimize noise. The controlled expiratory flow can also enable positive expiratory pressure (PEP) to be controlled. Some embodiments improve user comfort by having a locating pillow that helps to prevent the prongs from moving and rubbing on the inside of the nares. Because many of the interfaces described herein are similar to one another, any features not described in detail with respect to any particular embodiment can be the same as or similar to corresponding features of other embodiments described herein, or can be of any other suitable arrangement. Features of the various nasal interfaces can be combined together or interchanged with one another to form embodiments in addition to the particular embodiments shown.

FIGS. 1-6 illustrate several similar embodiments of a nasal interface 50 for supplying a flow of breathing gas from a flow generator 52 to a user or patient. The flow generator 52 can be of any suitable type, such as a ventilator or positive airway pressure device for example and without limitation. Optionally, the flow of breathing gas can be heated and/or humidified by a humidifier 54. Preferably, the nasal interface 50 includes a pair of laterally-extending arms or lateral arms 60 that support a first portion (e.g., a top part) of a frame 62 of the nasal interface 50, while an upper lip rest 64 supports a second portion (e.g., a lower part) of the frame 62 relative to the face of the user. The upper lip rest 64 may be similar to the lip rests disclosed in U.S. Patent Publication No. 2011/0146685, the entirety of which is incorporated by reference herein.

Figure 2:
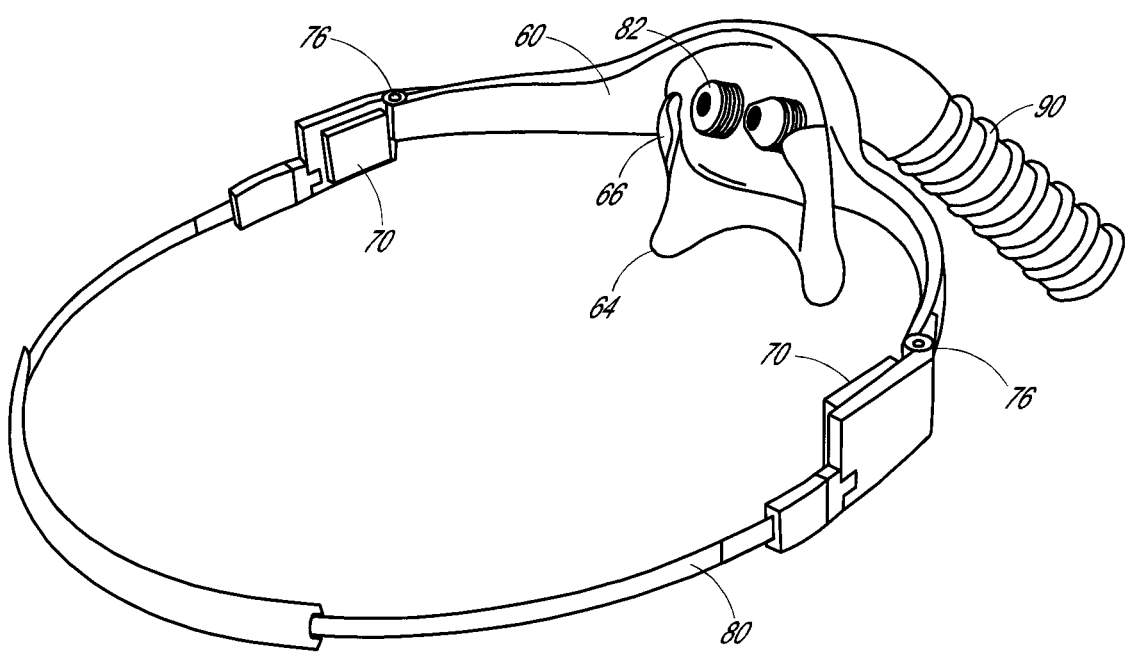
FIG. 2 is a rear perspective view of an alternative embodiment of a nasal interface.
Figure 3:
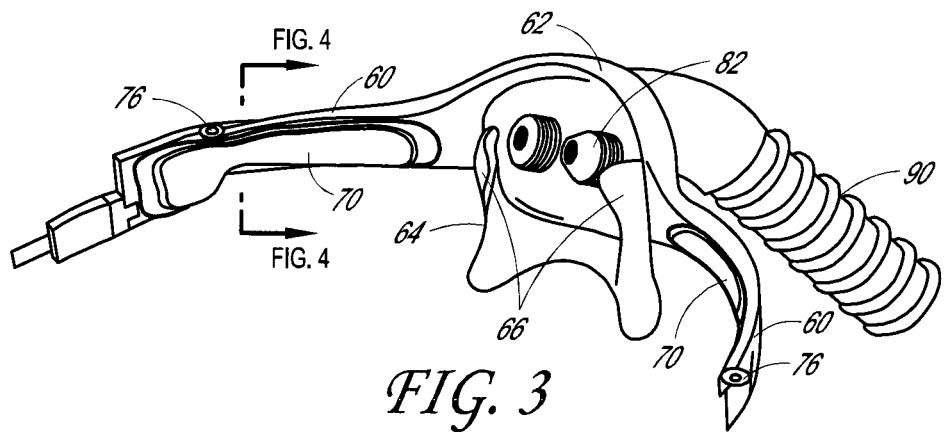
FIG. 3 is a partial rear perspective view of a yet another embodiment of a nasal interface.
Figure 5:
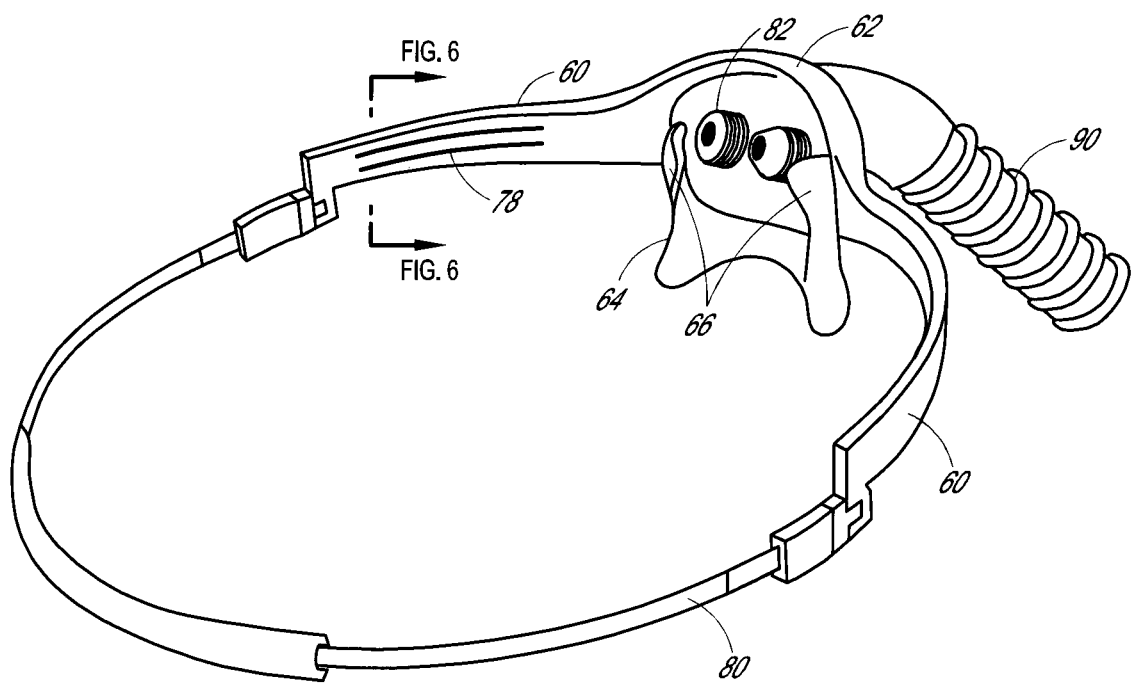
FIG. 5 is a rear perspective view of another embodiment of a nasal interface.

The lateral arms 60 of the frame 62 support the frame 62 and reduce pressure on the nose of the patient or keeps the frame 62 off the nose by loading a portion (e.g., the front) of the zygomatic bone (cheek bone) or a nearby or adjacent location. The lateral arms 60 may also have the function of locating the interface 50 or assisting in the location of the interface 50 laterally on the user's face by wrapping around the side of the zygomatic bone. With reference to FIGS. 2, 3 and 5, lateral support can be enhanced by the optional addition of an extension 66 from the upper lip rest 64 that sits near or adjacent the alar sidewalls of either side of the user's nose. Such a lip rest 64 can be used on any other embodiments of the interface 50 disclosed herein.

Figure 4:
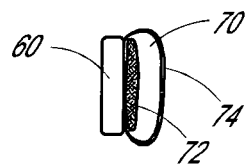
FIG. 4 is a sectional view of the nasal interface of FIG. 3 taken along line 4-4 in FIG. 3.

A soft pad 70 can be provided on an inner surface of each of the lateral arms 60 to provide comfort to the user. In some configurations, the pad 70 can be made from an absorbent or porous material to reduce heat buildup under the frame 62. The soft pad 70 can also be formed in an elongated manner as shown in FIGS. 3 and 4 to potentially contact both the front and side of the user's face. The pads 70 can be secured to the arms 60 by any suitable arrangement, such as an adhesive layer 72. The pads 70 can be constructed from any suitable material and may be homogeneous, such that the user-contacting or user-facing surface 74 is constructed from the same material as an interior portion of the pad 70, or may be heterogeneous, such that the surface 74 is constructed from a different material than an interior portion of the pad 70. The pads 70 may be made of a suitable soft material, such as a foam, gel or textile. In some arrangements, the pads 70 can be constructed from other suitable soft materials, such as a thermoplastic elastomer (TPE), silicone, or other similar materials.

Figure 6:
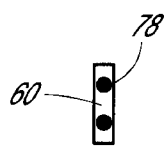
FIG. 6 is a sectional view of the nasal interface of FIG. 5 taken along line 6-6 in FIG. 5.

In some configurations, the lateral arms 60 are able to flex or adjust due to a suitable arrangement, such as a stiff or frictional hinge 76 shown in FIGS. 2 and 3 or a relatively rigid, formable material 78 as shown in the interface 50 of FIGS. 5 and 6. The formable material 78 can be of any suitable arrangement, such as metal wire 78 positioned on (FIG. 5) or embedded within (FIG. 6) the lateral arms 60. In other configurations, the formable material 78 can be filled plastic or any other deformable material that tends to hold its shape once deformed, so that a user can easily form the lateral arms 60 of the interface 50 to the width of his or her face for more comfort and/or security. The frame 62 can be secured to the user's head using any suitable retention device or headgear 80, such as an elastic strap (FIG. 1) or adjustable harness (FIGS. 2 and 5).

Advantageously, in at least some configurations, because the lateral arms 60 and upper lip rest 64 preferably support the mask frame 62 away from the nose, it becomes possible and/or practicable to utilize nasal locators or nasal delivery arrangements, which are referred to herein as nasal delivery elements 82, such as one of those shown in FIGS. 7a-7g. Preferably, a pair of nasal delivery elements 82 is provided with one for each nare of the user. However, arrangements are possible in which only a single nasal delivery element 82 is provided or in which no nasal delivery elements 82 are provided.

In some configurations (FIGS. 7a-7c and 70, the illustrated nasal delivery elements 82 include a nasal tube or prong 84. In some configurations (FIGS. 7a-7e), the nasal delivery elements 82 include a nasal pillow or seal element 86. In some configurations (e.g., FIGS. 7a-7c), the nasal delivery elements 82 include both a prong 84 and a seal element 86. The preferably concertina (e.g., accordion, bellows or corrugated) shape or other variable length or compressible shape of the seal elements 86 provides a spring force against the nares that preferably maintains a good seal even if the interface 50 moves slightly relative to the user's face. If desired, the optional inner tube or prong 84 can fit internally in the nares in combination with the concertina seal elements 86. Some uses and advantages of such an arrangement are discussed herein with respect to FIGS. 17 and 18. In addition, because there typically is direct contact between the upper surfaces of the concertina pillow 86 and the user's nare, the pillow 86 may act as a locating device for the inner cannula prong 84.

The term prong is used herein in accordance with its ordinary meaning and usually refers to a nasal tube or nasal element that does not itself create a complete seal with the nare of the user or is not designed to create a complete seal under normal conditions, including proper sizing of the prong, proper insertion of the prong into the nare or absence of external forces, for example. The term nasal pillow is used herein in accordance with its ordinary meaning and usually refers to a nasal element that creates a complete or substantially complete seal with the nare of the user or is designed to create a complete or substantially complete seal under normal conditions. A nasal pillow can include a tube portion or prong portion that enters the nare of the user; however, this portion typically does not itself create a seal. The term nasal delivery element, as used herein, can refer to a prong, a pillow, a combination of the two or any other nasal element or nasal locator, unless indicated otherwise.

Figure 7A:
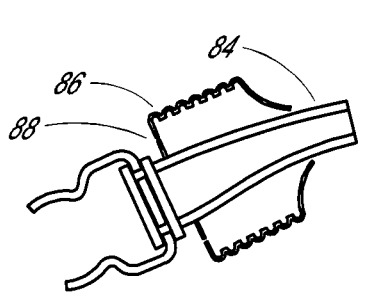
FIGS. 7a-7g are views of several nasal prong assemblies that can be used with the nasal interfaces disclosed herein.
Figure 7D:
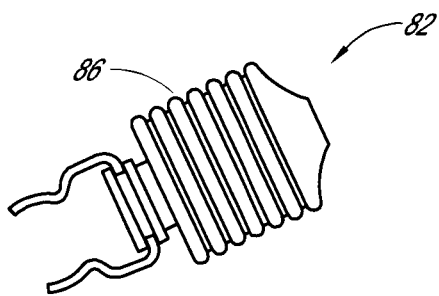

With reference to FIG. 7a, the seal element 86 can include one or more exhaust vents 88 that permit gas to be evacuated from an interior of the seal element 86 when an upper surface of the seal element 86 is sealed against the nose of a user. Such an arrangement can be used as an expiratory pressure maintenance device because it would seal the nares which would increase the pressure inside the user's airways. The pressure within the user's airways can be controlled by designing the exhaust vent(s) 88 to provide a certain flow rate and thus maintain a specified or suitable pressure (or pressure range) within the airways. The exhaust vent 88 can also provide a means of flushing $CO_2$, which is not a problem with traditional unsealed cannula designs.

In particular, FIG. 7a illustrates one possible arrangement of a bias flow vent is illustrated in which one or more apertures 88 are provided, for example, at the bottom of the concertina pillow 86. Exhaled air will pass between the inner tube/prong 84 and the pillow 86 into the chamber created by the concertina pillow 86 and will then exit through the one or more apertures 88 to the atmosphere. The size and number of apertures 88 will determine the rate at which exhaled air is expelled from the chamber and will thus influence the pressure build up within the user's airways. In addition, the aperture(s) 88 can be provided in other locations on the pillow 86 (e.g., the side) or other vent arrangements can be used, such as the outlet 92 described hereinafter.

Figure 7B:
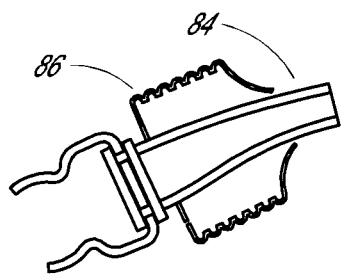
Figure 7E:
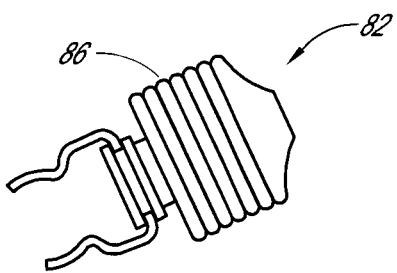
Figure 7C:
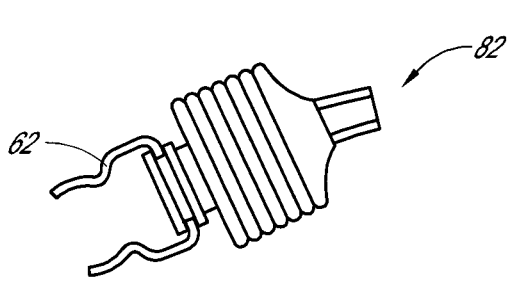
Figure 7F:
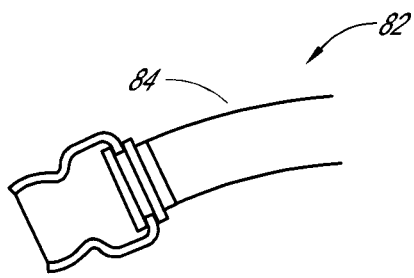

An upper portion of the seal element 86 can be loose around the prong 84 such that a gap exists between the seal element 86 and the prong 84, as illustrated in FIGS. 7a and 7b, or the upper portion of the seal element 86 can fit tightly and/or seal against an exterior surface of the prong 84, as illustrated in FIG. 7c. A length of the seal element 86 can be selected relative to the prong 84 such that an end portion of the prong 84 is exposed from the seal element 86, as illustrated in FIGS. 7a-7c. Alternatively, the seal element 86 can be the same length (or longer) than the prong 84 in the uncompressed orientation.

Figure 7G:
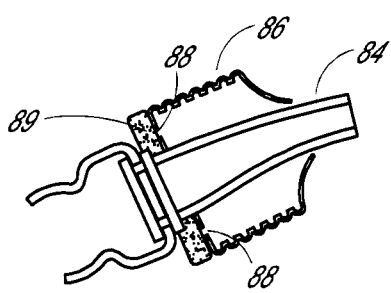
Figure 8:
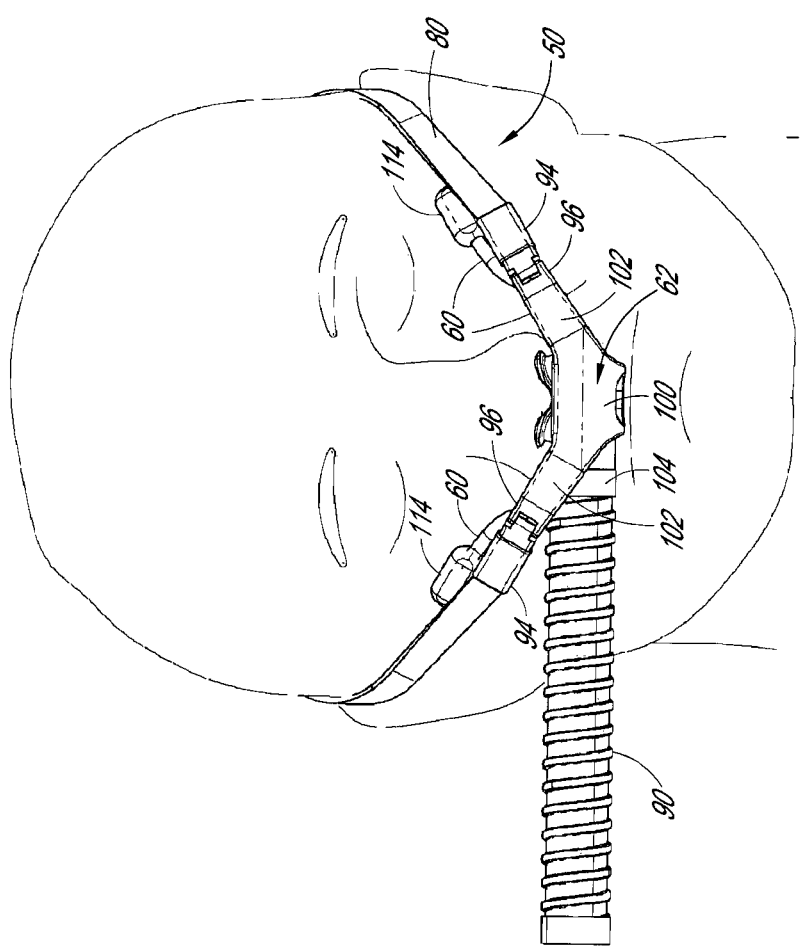
FIG. 8 is a front view of another embodiment of a nasal interface positioned on a user.
Figure 9:
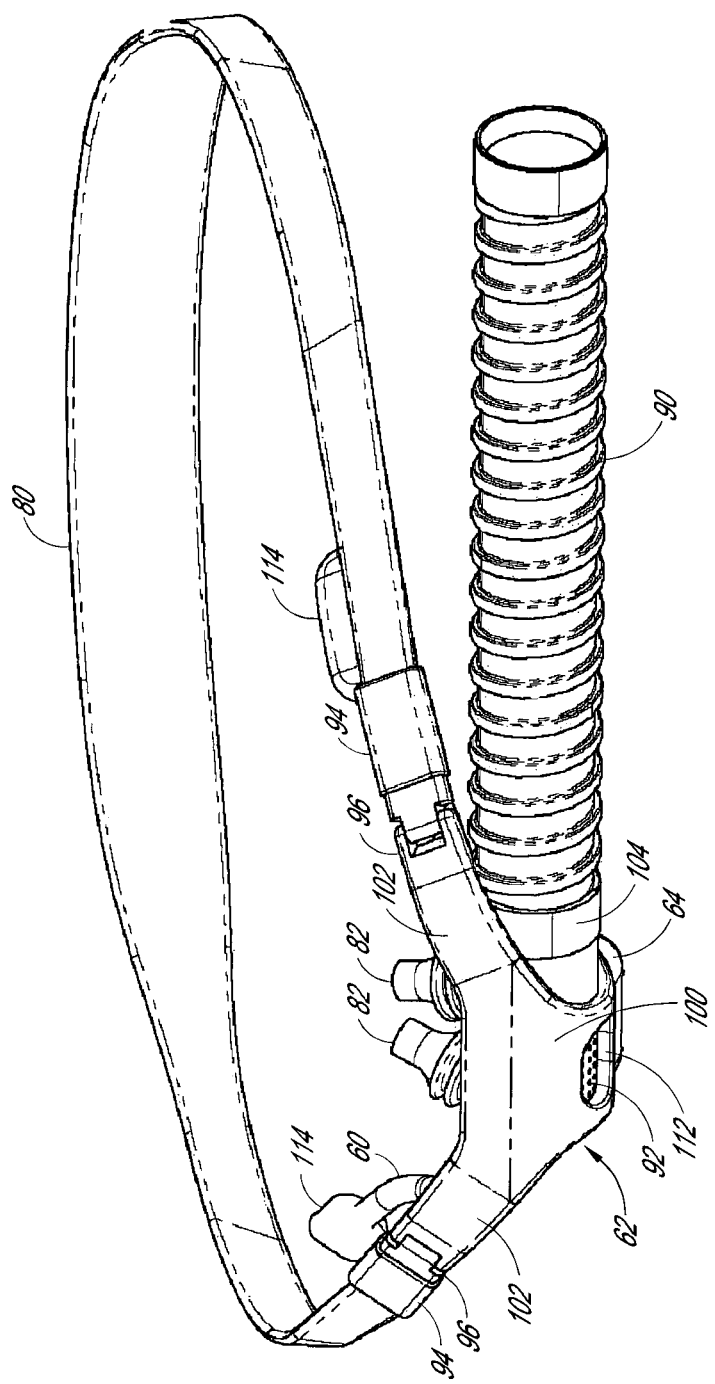
FIG. 9 is a front perspective view of the nasal interface of FIG. 8 with a breathing tube oriented to exit on the left side of the nasal interface.
Figure 10:
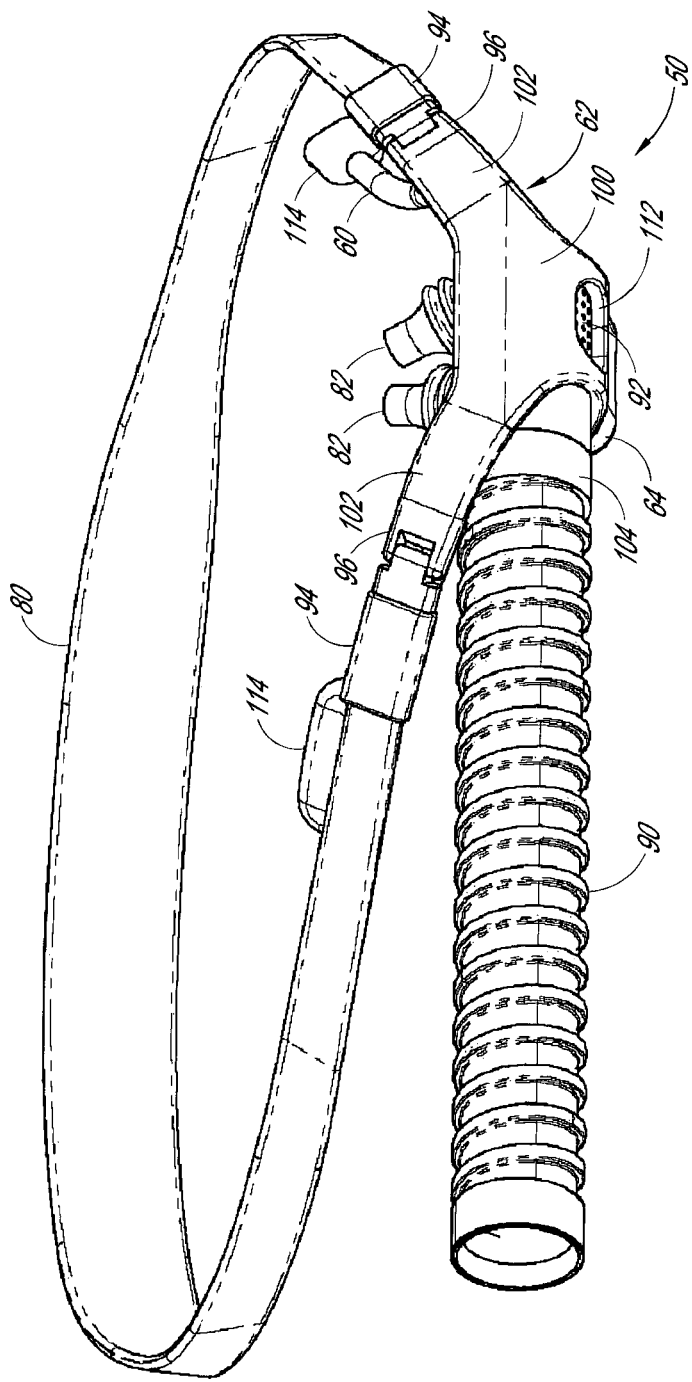
FIG. 10 is a front perspective view of the nasal interface of FIG. 8 with the breathing tube oriented to exit on the right side of the nasal interface.
Figure 11:
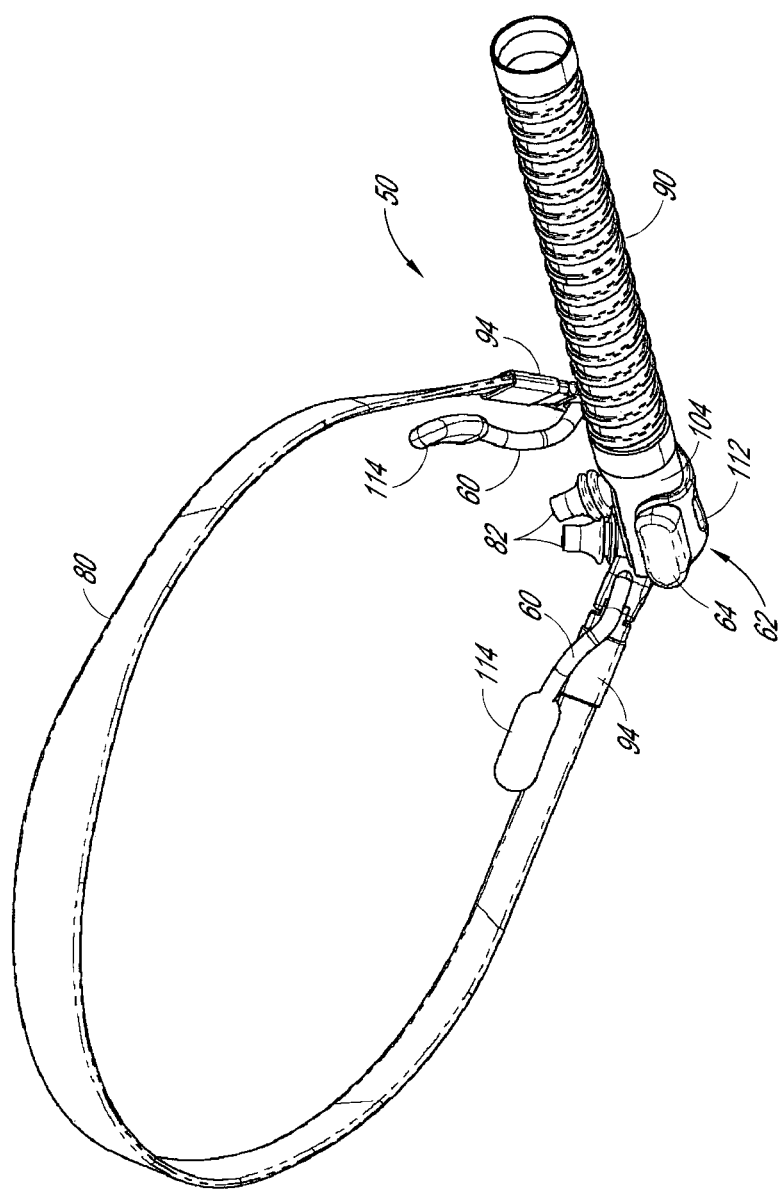
FIG. 11 is a rear perspective view of the nasal interface of FIG. 10.
Figure 12:
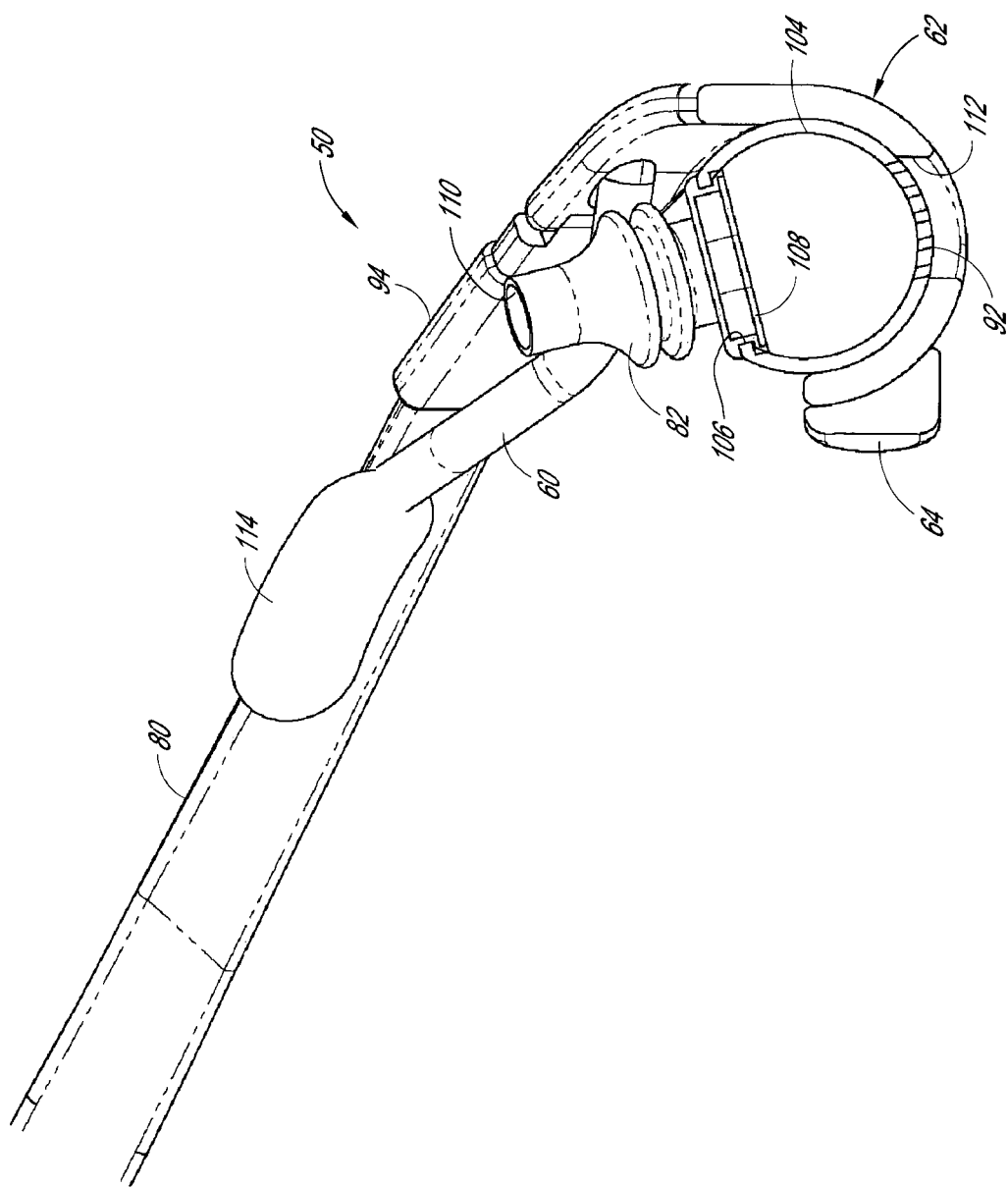
FIG. 12 is a sectional view of the nasal interface of FIG. 8 taken along line 12-12 in FIG. 8 between nasal elements of the nasal interface.
Figure 13:
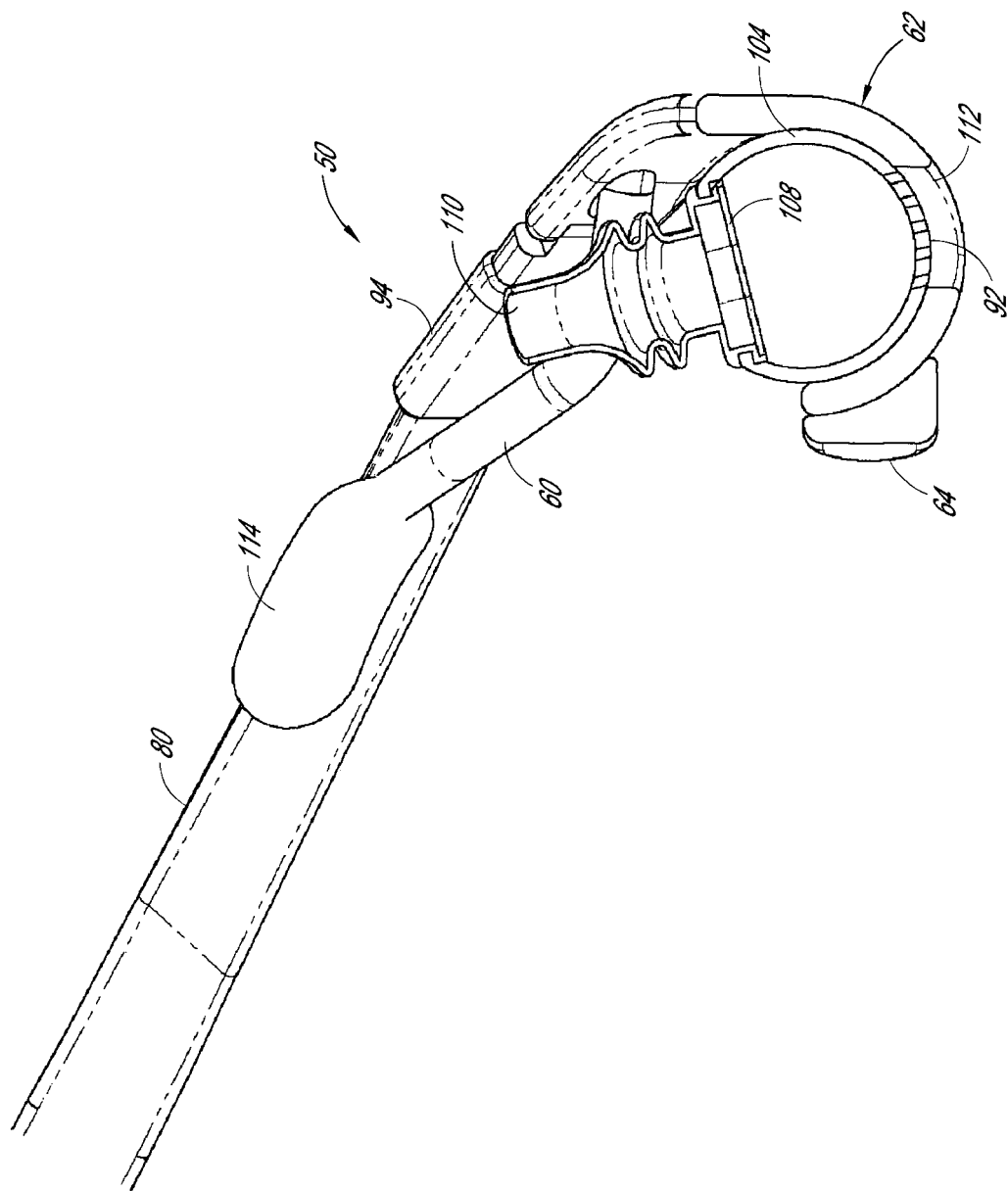
FIG. 13 is a sectional view of the nasal interface of FIG. 8 taken along line 13-13 in FIG. 8 through a nasal element of the nasal interface.

FIG. 7g illustrates a nasal delivery element 82 similar to that of FIG. 7a including a vent 88 in the seal element 86. However, the nasal delivery element 82 of FIG. 7g includes a diffuser element 89 that covers the exhaust vent 88. In the illustrated arrangement, the diffuser element 89 is in the form of a disk or annular structure made from foam or another suitable porous material to help reduce or minimize draft and noise from the exhaust vent 88. The diffuser 89 can be located on the distal side of the concertina pillow 86 between a base of the prong 84 and the bottom surface of the pillow 86. In alternative configurations, other suitable types of diffuser elements and/or other locations can be utilized.

The selection of the specific type or design of nasal delivery element 82 generally will be dictated by the particular use of the nasal interface 50. In many instances, if the interface 50 is to be used for CPAP treatment, then it is often desirable to have the outer concertina pillow 86 as it creates the seal to generate pressure in the user's airway. For high-flow therapy (HFT), any of the described nasal delivery elements 82 may be used; however where the embodiments that include the concertina pillows 86 are used there preferably will be a bias flow vent (e.g., exhaust vent 88 or outlet 92—described hereinafter) incorporated in the interface 50, which is generally not required when only the inner tube prongs 84 are used.

Another advantageous feature of certain preferred embodiments is the use of the concertina (or other) seal elements 86 and inner tube or prong 84 combination as an expiratory pressure maintenance device. Nasal tubes or prongs 84 can be utilised on their own (e.g. without the seal elements 86) to avoid creating a seal with the user's nares in order to provide a leak space for high flow therapies. However, an arrangement that creates a seal with the user's nose and has a controlled exhaust vent (e.g. the exhaust vent 88, the outlet 92 described hereinafter or any other suitable arrangements) can be used to maintain a positive expiratory pressure. Maintaining a positive expiratory pressure (PEP) may be beneficial to COPD patients in relieving shortness of breath by helping to slow down breathing rates, improving airway patency and the ability to expire gasses from the lung. The exhaust vent 88 can also be useful for CPAP treatment as it provides bias flow with a significantly reduced dead space in an interface design.

The nasal delivery elements 82 are fluidly coupled to a conduit or supply tube 90 that delivers the flow of breathing gas from the flow generator 52 to the nasal interface 50. The supply tube 90 can be a suitable, flexible tube of a wound construction or extruded construction, for example and without limitation. As shown in FIG. 1, the nasal interface 50 can also include an outlet 92, such as a bias flow outlet or bias flow openings, to permit an unused portion of the flow of breathing gas and/or patient expiration gases to exit the interface 50.

In the illustrated configurations, the nasal delivery elements 82 preferably can be removed and replaced on the frame 62, such as by a snap fit or opening-and-groove arrangement, as illustrated in FIGS. 7a-7f. Thus, preferably, the nasal delivery elements 82 can be individually removed and replaced. In other configurations, both nasal delivery elements 82 can be removed and replaced as a unit or can be permanently secured to the frame 62 or other portion of the interface 50.

FIGS. 8-15 illustrate an embodiment of a nasal interface 50 sharing similarities with the previously-described interfaces 50. The nasal interface 50 includes a frame portion or frame 62 and a suitable headgear 80 to secure the frame 62 to the user. The headgear 80 can be of any suitable arrangement, such as a stretchable headband or generally non-stretchable headband incorporating an adjustment mechanism (not shown), for example and without limitation. The headgear 80 can be coupled to the frame 62 in any suitable manner, such as a hook-and-loop arrangement in which ends of the headband 80 includes hooks or clips 94 that can be engaged with openings defined by loop portions 96 of the frame 62.

In the illustrated configuration, the frame 62 is constructed from generally rigid material and is generally V-shaped or generally shaped like a chevron from a front view. The frame 62 has a central portion 100 and a pair of lateral side portions 102 that extend laterally and upwardly from the central portion 100. In some configurations, the lateral side portions 102 extend in a rearward direction from the central portion 100. Outward or rearward ends of the lateral side portions 102 define the loop portions 96. The upwardly directed lateral side portions 102 can direct the headband 80 upwardly from a position below the nose to above the ears of the user.

The central portion 100 of the frame 62 can be configured to support one or preferably a pair of nasal delivery elements 82. In particular, in the illustrated configuration, the nasal delivery elements 82 are directly supported by a manifold 104 that defines or is coupled to a patient or interface end of a supply tube 90. The manifold 104 preferably is constructed from a relatively rigid material and can be removably secured to the central portion 100, such as through a snap-fit, friction-fit or other suitable arrangement. In the illustrated arrangement, the central portion 100 is generally U-shaped from a side view, or is generally in the form of a cradle, and is sized to receive the manifold 104 in a friction-fit or snap-fit arrangement. In some configurations, there can be a slight undercut in the frame 62 that enables the manifold tube 104 to be held in place.

Preferably, the manifold 104 can be assembled to the central portion 100 of the frame 62 in two different orientations. In particular, in a first orientation, the supply tube 90 can extend in a first direction (e.g., to the right—FIGS. 8, 10 and 11) from the frame 62 and, in a second orientation, the supply tube 90 can extend in a second direction (e.g., to the left—FIG. 9) from the frame 62. Advantageously, with such an arrangement, the user can select a desirable orientation for the supply tube 90. The outer ends or loop portions 96 can be positioned above an upper edge of the supply tube 90 to avoid interference between the headband 80 and the supply tube 90. As described previously, the supply tube 90 can be connectable to a source of breathing gas via a suitable connector (e.g., swivel connector), which can be overmolded, threaded on or otherwise suitably coupled to an upstream end of the supply tube 90.

The illustrated manifold 104 preferably is a tube having a closed end and an open end coupled to a downstream or interface-end of the supply tube 90. A sidewall of the tube 104 defines an opening 106, which is configured to receive an insert 108 containing the pair of nasal delivery elements 82. In some configurations, the insert 108 is symmetrical and can be inserted in either orientation. Alternatively, each nasal delivery element 82 (or a single nasal delivery element 82) can be separately secured to the tube 104 or the tube 104 (or other permutation of the manifold 104) and the nasal delivery elements 82 can be unitarily-formed. The insert 108 can be coupled to the opening 106 by any suitable arrangement, such as a lip-and-groove arrangement as shown. The nasal delivery elements 82 can be unitarily-formed with the insert 108 or can be otherwise secured to the insert 108. The nasal delivery elements 82 define passages 110 that communicate with an interior space of the tube 104 such that breathing gas can pass from the supply tube 90 to the user through the nasal delivery elements 82. As described previously, the nasal delivery elements 82 can comprise nasal prongs, nasal pillows or a combination of prongs and pillows. In the illustrated arrangement, the insert 108 comprises nasal pillows that are configured to create a seal with the nares of the user.

In the illustrated arrangement, the sidewall of the tube 104 defines an outlet 92 that cooperates with an outlet or opening 112 of the frame 62. Preferably, the outlet 92 of the tube 104 is located opposite the opening 106 that supports the insert 108 and, thus, is located opposite the nasal delivery elements 82. The outlet 92 can also be axially aligned with the opening 106. In the illustrated arrangement, the outlet 92 is a bias flow outlet comprising a plurality of relatively small-diameter openings. The outlet 92 is aligned with the opening 112 of the frame 62 when the tube/manifold 104 is properly positioned in the frame 62. Preferably, the opening 112 is sized in a circumferential direction (e.g., made larger than the outlet 92) so that the manifold 104 can be rotated relative to the frame 62 and the outlet 92 and opening 112 will remain sufficiently aligned for use thus permitting some range of angular adjustment of the nasal delivery elements 82. In alternative arrangements, the manifold 104 can include an opening and the frame 62 can include bias flow holes. Other suitable arrangements for allowing gases to exit the manifold 104 can also be employed.

Similar to the previously-described interfaces, the nasal interface 50 of FIGS. 8-15 include lateral support elements configured to contact lateral locations on the face of a user. In the illustrated configuration, the support elements are in the form of lateral arms 60 that extend in opposite lateral directions and, preferably, rearwardly from the frame 62. Preferably, a first end of each arm 60 is secured to the frame 62 and a second or free end preferably includes a pad 114 that, in use, contacts a lateral location on the face of the user. Preferably, the supports are bendable or formable members that permit a position of the pads 114 to be customized by a user. The illustrated arms 60 can comprise or be in the form of bendable wire-reinforced stalks (e.g., formable wire members embedded in a surrounding material) that permit adjustment of a position of the pads 114. However, other suitable support arrangements for the pads 114 can also be used.

The pads 114 can, include or be constructed from a suitable soft material, such as a thermoplastic elastomer (TPE), silicone, or other similar materials. The pads 114 can be removable and/or replaceable, if desired. Preferably, each of the pads 114 is spaced from a centerline of the interface 50 a sufficient distance to help inhibit or prevent lateral movement of the nasal delivery elements 82. In the illustrated arrangement, the pads 114 are positioned outwardly of outer edges of the frame or outwardly of outer ends of the lateral arms 60.

The illustrated interface 50 also includes an upper lip support or upper lip rest 64 that is supported by the frame 62 and, in use, contacts the face of a user at a location on the upper lip between the mouth and the nose. The lip rest pad 64 can be made from a suitable preferably soft material, such as silicone or TPE. The lip rest pad 64 can be removable and/or replaceable, if desired. The lip rest pad 64 creates a third point of contact on the user's face, in combination with the cheek pads 114, which increases both lateral and rotational stability of the interface 50. In the illustrated configuration, the lip rest pad 64 is secured to a rearward portion of the central portion 100 of the frame 62 and defines a rearward-facing user contact surface. Preferably, the cheek pads 114 and lip rest pad 64 define three discrete areas of contact (e.g., two upper areas and a lower area) for supporting the frame 62 relative to the user. Preferably, the frame 62 does riot otherwise contact the face of the user. In addition, except for inadvertent contact from the supply tube 90, preferably the illustrated nasal interface 50 only contacts the face of the user at the three discrete areas of contact, the nasal delivery element(s) 82 and the headband or other headgear 80.

Figure 16:
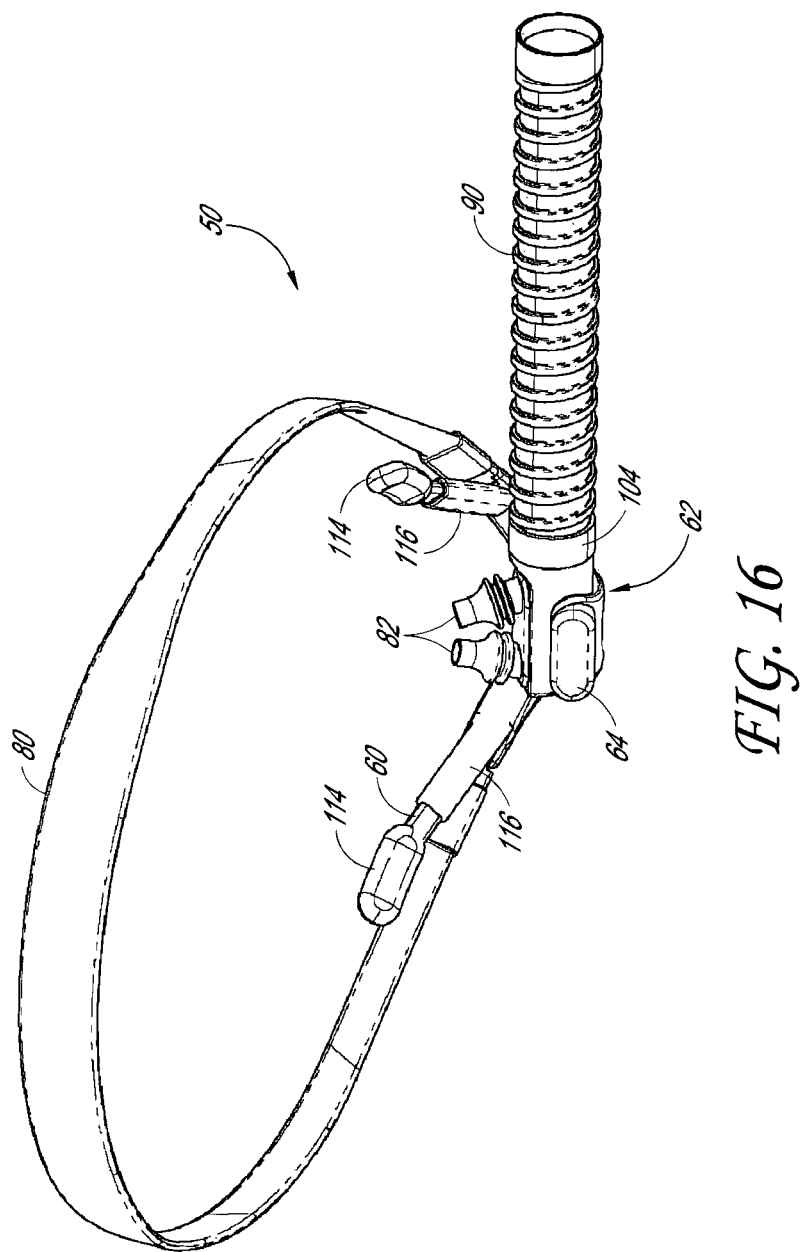
FIG. 16 is a rear view of another embodiment of a nasal interface similar to the embodiment of FIG. 8 with adjustable arms or sleeves positioned on the arms.

With reference to FIG. 16, a modification of the nasal interface 50 of FIGS. 8-15 is shown. The lateral arms 60 of the nasal interface 50 of FIG. 16 each include a sleeve 116 that forms a portion of or surrounds the lateral arm 60. In one configuration, the sleeve 116 is secured to the frame 62 and forms a proximal or frame-connecting portion of the lateral arm 60. The sleeve 116 supports a distal or pad-supporting portion of the lateral arm 60 for movement relative to the sleeve 116 (e.g., sliding or telescopic movement) to permit adjustment of an overall length of the lateral arm 60. Although the sleeve 116 surrounds the remaining portion of the lateral arm 60 in the illustrated arrangement, the arrangement could be reversed with the distal portion of the lateral arm 60 surrounding the proximal portion. Other alternative length-adjustable arrangements could also be employed on this or the other embodiments disclosed herein.

Alternatively, the sleeve 116 can be in the form of a cover for the lateral arm 60, which can be constructed from a softer material than the underlying lateral arm 60 to improve comfort for the user. The sleeve 116 can completely or partially encircle the lateral arm 60 and can be made of materials the same as or similar to those described herein with respect to the soft pads 70 (e.g., silicone, a soft fabric, etc.). The sleeve 116 can be removable and/or replaceable. If the sleeve 116 fully encircles the arm 60, it can simply be retained on the lateral arm 60 by being too small to easily or inadvertently slide over the pad 114. The sleeve 116 could be removed by being stretched over the pad 114 or could include a seam closable by a suitable fastener (e.g., hook-and-loop fastener) that can be opened to permit removal. Alternatively, the sleeve 116 can be adhered to the lateral arm 60 with a suitable adhesive, which can be reusable, if desired. Such a sleeve 116 can be used to provide additional user comfort on any of the embodiments herein.

FIGS. 17 and 18 illustrate a modification of the supply tube 90 and manifold 104 assembly of FIGS. 14 and 15. The assembly of FIGS. 17 and 18 defines an inspiration or inhalation flow path that is separated from an expiration or exhalation flow path. In some instances, it can be beneficial to have separate inspiratory and expiratory flow paths when a sealed pillow 86 arrangement is used for high flow therapy (HFT) to help transfer some of the heat and moisture associated with HFT away from the user's face. When non-sealing or not-fully-sealing prongs are used for HFT, heat and moisture are dispersed via the open flow of air from the nostrils of the user. Accordingly, if the nares are sealed by pillows 86, it is advantageous to provide a separate flow path for the heat and moisture to escape to reduce or prevent discomfort to the user. As discussed previously, another advantage made possible by using a seal element 86 and inner tube or prong 84 in combination is the ability to maintain expiratory pressure. For example, an arrangement that creates a seal with the user's nose can have a controlled exhaust vent (e.g. the exhaust vent 89, the outlet 92 described hereinafter or any other suitable arrangements) that maintains a positive expiratory pressure. This may be beneficial to COPD patients in relieving shortness of breath by helping to slow down breathing rates, preventing airway collapse and increasing the efficiency of each breath by helping to flush old air from the lungs. The exhaust vent can also be useful for CPAP treatment as it provides bias flow with a significantly reduced dead space in an interface design.

In the illustrated arrangement, a divider 120 is positioned within the manifold 104 to separate an interior space of the manifold 104 into an inspiration flow portion 122 and an expiration flow portion 124. In the illustrated configuration, the divider 120 has a generally cylindrical sidewall 126 that extends in a longitudinal direction or along a longitudinal axis of the manifold 104 and may be generally coaxial with the manifold 104. The divider 120 also includes an annular end wall 128 that creates at least a substantial seal with an interior surface of the manifold 104 and permits fluid communication between the supply tube 90 and the interior space of the divider 120. However, the end wall 128 at least substantially prevents fluid communication between the supply tube 90 and the space within the manifold 104 exterior of the divider 120. Accordingly, at least a portion of the inspiration flow portion 122 is defined within the sidewall 126 and at least a portion of the expiration flow portion 124 is defined outside of the sidewall 126. Although a generally coaxial arrangement is illustrated, other compartmentalized or other arrangements that separate the inspiration flow portion 122 and the expiration flow portion 124 can be employed.

Preferably, the nasal delivery elements 82 define separated inspiration and expiration flow paths 130 and 132, respectively. In the illustrated arrangement, the nasal delivery elements 82 each include a prong 84 and a seal element or pillow 86. One of the prong 84 and seal element 86 defines the inspiration flow path 130 and the other of the prong 84 and seal element 86 defines the expiration flow path 132. In the illustrated arrangement, the prong 84 communicates with the interior space or inspiration flow portion 122 of the divider 120 and, thus, defines the inspiration flow path 130. The prongs 84 can be coupled to the divider 120 by any suitable arrangement, including the unitary configuration illustrated. Preferably, the seal elements 86 surround and can be substantially coaxial with their respective prong 84. The seal elements 86 can be coupled to the manifold 104 by a suitable arrangement, such as being unitarily formed with one or more inserts 108, as described previously. The expiration flow paths 132 of the seal elements 86 (defined between the outer surfaces of the prongs 84 and the inner surfaces of the seal elements 86) communicate with the expiration flow portion 124 of the interior space of the manifold 104. An outlet, such as a bias flow outlet or bias flow holes 92, allows expiratory gases to exit the manifold 104.

Advantageously, such an arrangement in which internal prongs define an inwards air supply path and external pillow structures define a separated exhaust path is well-suited for use in high flow therapies. In particular, the seal element or pillow 86 is designed to seal the user's nare thereby forcing all or substantially all air exhaled via the nose to follow the defined exhaust path. This is beneficial in that allows the expiratory flow to be controlled, which can help to minimize noise. In addition, the external pillow structure provides stability to the prongs and improves comfort for the user.

Figure 19:
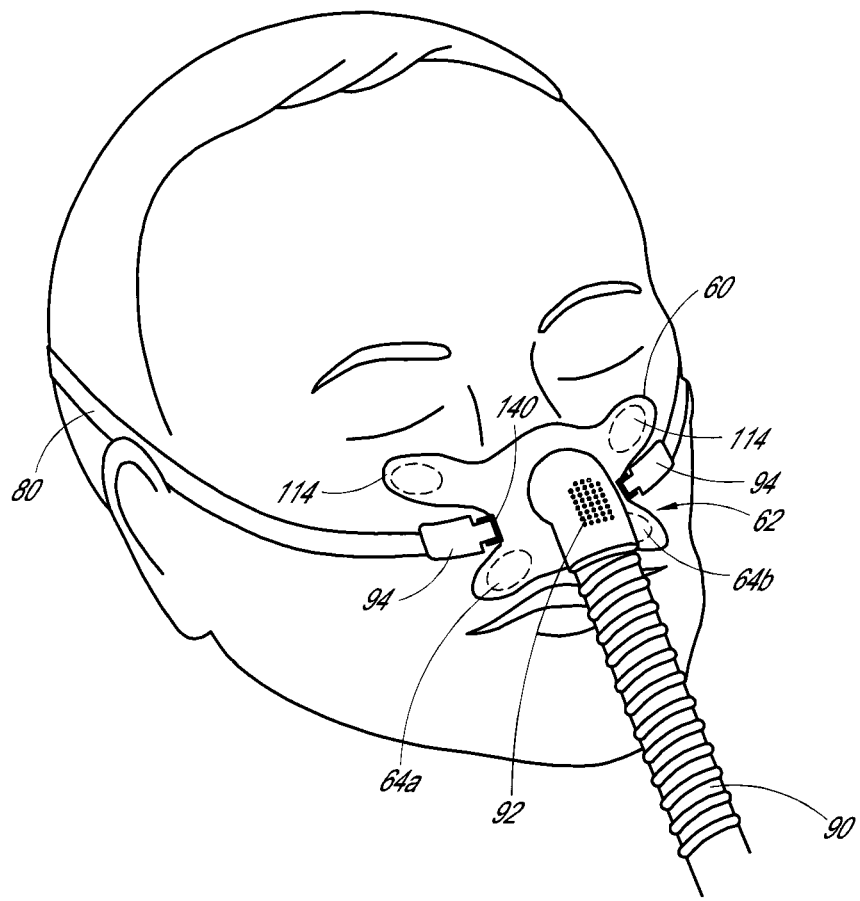
FIG. 19 is a front perspective view of another embodiment of a nasal interface positioned on a user.

FIG. 19 illustrates a nasal interface 50 that is similar to the previously-described interfaces, in particular, those of FIGS. 1-6. However, the nasal interface 50 of FIG. 19 preferably includes lateral arms 60 that have a narrower stance, or define a smaller lateral distance between their respective user-contacting surfaces, relative to the previously-described interfaces 50. In addition, although the nasal interface 50 of FIG. 19 could include a single lip-contact area or lip rest 64, the illustrated interface comprises a pair of lip rest areas 64a and 64b, which preferably are discrete from one another. In particular, the nasal interface 50 of FIG. 19 preferably includes a semi-rigid or rigid frame 62 with four stabilizing pads, which can be defined by the pair of upper pads or cheek pads 114 and the pair of lip rest pads 64a and 64b. The pads 64a, 64b, 114a, 114b can be located in a cross formation where there are two upper pads (114) and two lower pads (64a, 64b). The upper pads 114a, 114b can rest in the general region of or near the zygomatic bones. Preferably, the upper pads 114a, 114b are positioned laterally inward of the zygomatic bones and next to the nasal flanks and/or directly below the eyes. In some configurations, the pads 114a, 114b can be located at or near an inner portion of the cheek beside the lateral cartilage. Preferably, the lower pads 64a, 64b rest on the maxilla above the user's lips. In some configurations, at least the outer edges of the lower pads 64a, 64b are located outwardly of the user's nose (laterally beyond the alar sidewalls). In some configurations, the outer edges or outer portions of the lower pads 64a, 64b can be located at or near the corners of the user's mouth. In some configurations, the upper pads 114, 114 can be spaced further apart than the lower pads 64a, 64b.

Advantageously, such an arrangement of stability pads 64a, 64b, 114, 114, preferably in combination with headgear attachment points or locations 140 between the headgear 80 and the frame 62 that are located between the upper pads 114, 114 and the lower pads 64a, 64b provides rotational stability for the nasal interface 50. In some configurations, the attachment points or locations 140 may be located on or near a vertical centerline of the frame 62 or on or near a centerline equidistant from the upper pads 114, 114 and the lower pads 64a, 64b. In some configurations, the frame 62 can have recessed side portions between the upper pads 114, 114 and the lower pads 64a, 64b to accommodate the hooks or clips 94 or other headgear attachment components. As with one or more of the other interfaces disclosed herein, the contact locations or stability pads 64a, 64b, 114, 114 can space the frame 62 away from the user's face preferably such that no other portion of the frame 62 makes substantial contact with the user's face or applies substantial pressure to the user's face. Frame 62 provides a stable platform away from the nose from which gas delivery prongs and or seal elements can be located. This allows the sealing force to be controlled by the seal element design and not the headgear. Any combination of nasal delivery elements 82 and/or types of headgear 80 disclosed herein, or is otherwise suitable, can be used with the interface arrangement of FIG. 19.

Figure 20:
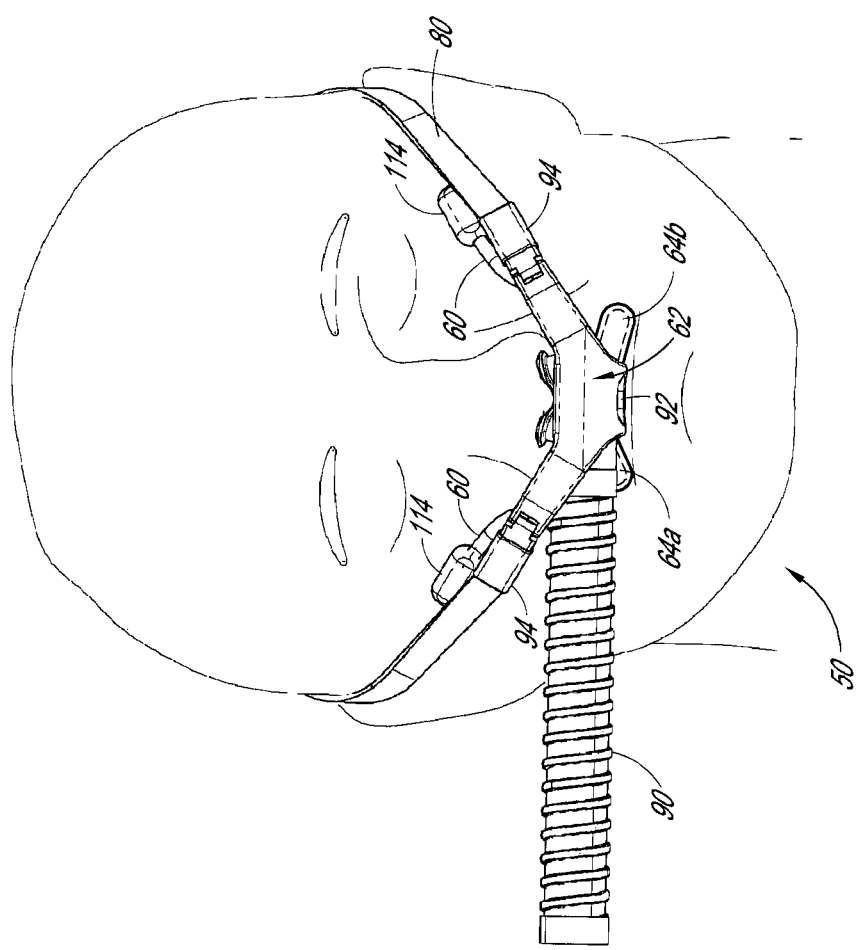
FIG. 20 is a front view of another embodiment of a nasal interface positioned on a user.

FIG. 20 illustrates a nasal interface 50 that is similar to the previously-described interfaces, in particular, those of FIGS. 8-15. However, the nasal interface 50 of FIG. 20 preferably includes four points or areas of contact similar to the interface described with reference to FIG. 19. Thus, preferably, instead of a single central lip pad, there are two pads 64a, 64b that sit on the user's upper lip but towards the corners of the mouth. Such an arrangement can be beneficial in providing increased lateral stability and spreading load forces over a greater area. Having a single load point or area at the center of the upper lip can be uncomfortable to some users. Accordingly, distributing the load to the sides of the lip may improve comfort. Similar to the interface of FIG. 19, the upper pads 114, 114 can be spaced further apart than the lower pads 64a, 64b. Moreover, the headgear attachment points or locations 140 can be located between the upper pads 114, 114 and the lower pads 64a, 64b in vertical and/or horizontal directions and on or near a centerline equidistant from the upper pads 114, 114 and the lower pads 64a, 64b. Furthermore, the contact locations or stability pads 64a, 64b, 114, 114 can space the frame 62 away from the user's face preferably such that no portion of the frame 62 makes substantial contact with the user's face or applies substantial pressure to the user's face. Any combination of nasal delivery elements 82 and/or types of headgear 80 disclosed herein, or is otherwise suitable, can be used with the interface arrangement of FIG. 20.

Figure 21:
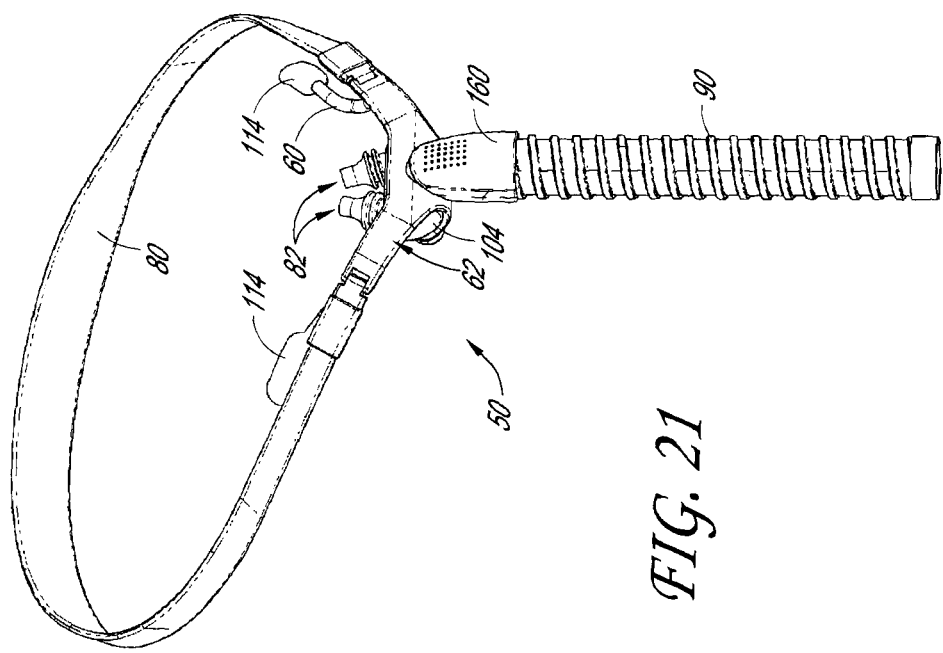
FIG. 21 is a front perspective view of another embodiment of a nasal interface.
Figure 22:
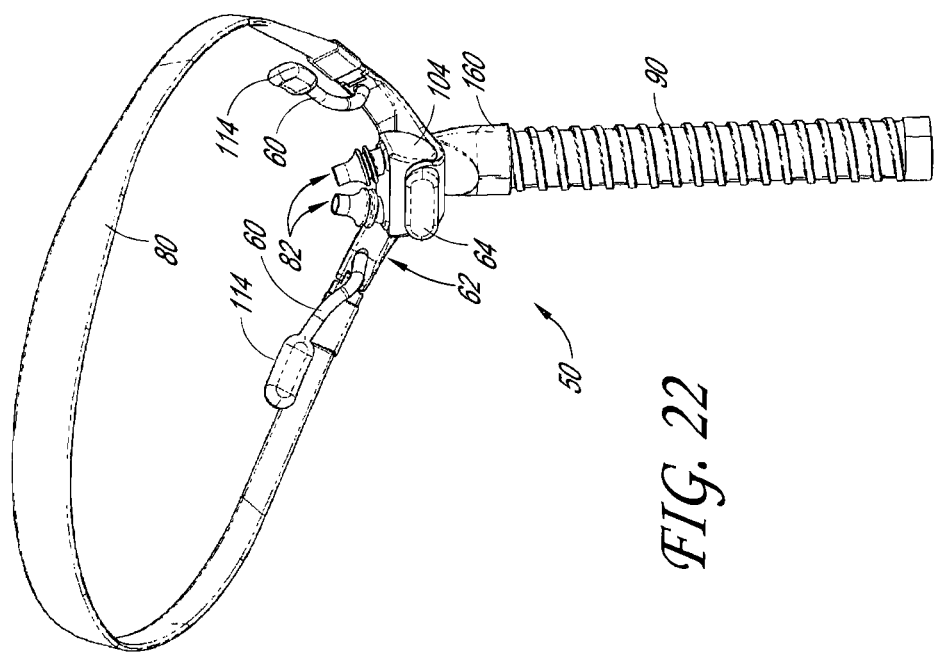
FIG. 22 is a rear perspective view of the nasal interface of FIG. 21.

FIGS. 21 and 22 illustrate a nasal interface 50 that is similar to the previously-described interfaces, in particular, those of FIGS. 8-15. However, the nasal interface 50 of FIGS. 21 and 22 includes a non-directional or, preferably, centrally-located connector or elbow 160 that couples the supply tube 90 to the nasal delivery elements 82 (via the manifold 104) for fluid communication. Preferably, the elbow 160 is pivotal relative to the frame 62 of the nasal interface 50 about at least one axis of rotation. In some configurations, the elbow can be a ball elbow 160 comprising a ball joint arrangement that provides for pivotal movement about two axes of rotation. The elbow 160 can be coupled directly to the manifold 104 (via an access opening in the frame 62, which can allow for rotational adjustment of the manifold 104 and nasal delivery elements 82 relative to the frame 62) or can be coupled to the frame 62 and be capable of fluid communication with the manifold 104 via intervening structure, such as an opening defined by the frame 62. Other suitable arrangements can also be employed to couple the elbow 160 for fluid communication with the nasal delivery elements 82. Such an arrangement can be beneficial for when the interface is used for PAP (e.g., CPAP) treatment as it will help to reduce or minimize hose drag. Such an arrangement can also allow the patient more freedom in movement as the supply tube 90 and supply conduit or tube are not oriented in any particular direction.

Figure 23:
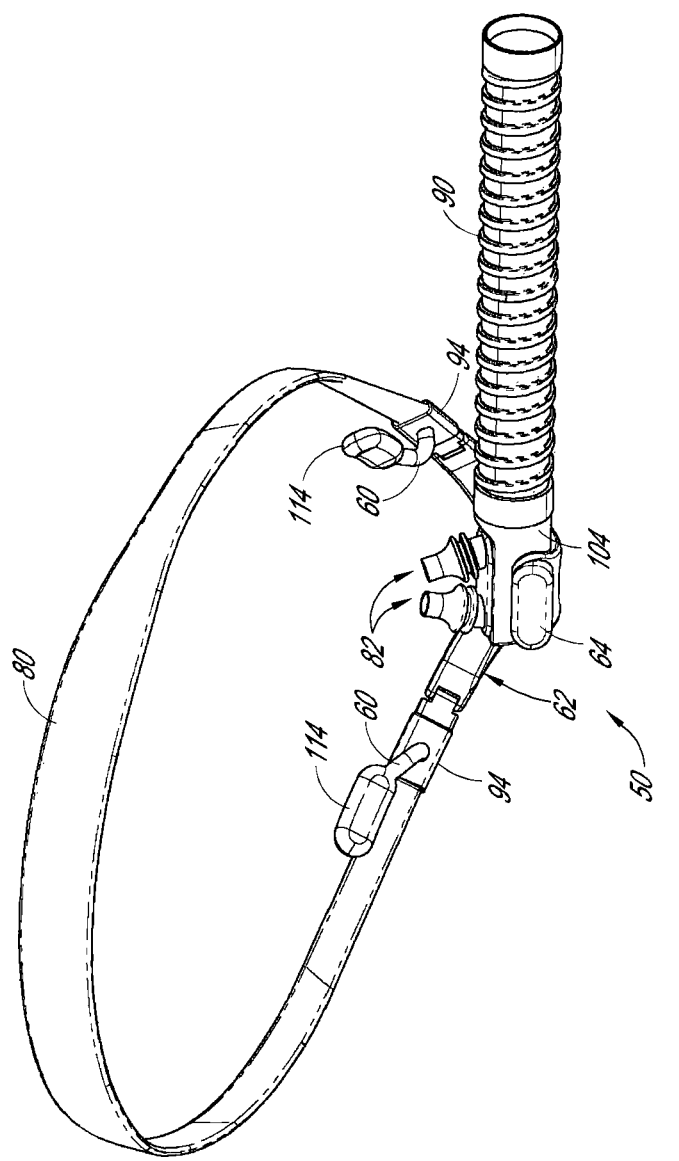
FIG. 23 is a rear perspective view of another embodiment of a nasal interface.

FIG. 23 illustrates a nasal interface 50 similar to the previously-described interfaces, in particular, those of FIGS. 8-15. However, in the nasal interface 50 of FIG. 23, the lateral arms 60 are carried by the headband or other headgear 80. In particular, the lateral arms 60 are coupled to and extend from an attachment portion, such as the hooks or clips 94 of the headband 80. The lateral arms 60 can be sized such that the resulting position of the user-contacting portions or pads 114 is similar to or the same as those of the previously-described interfaces. Thus, the lateral arms 60 of the interface 50 of FIG. 23 can be shorter than the prior lateral arms 60 anchored on the frame 62. Such an arrangement can help to keep the headgear clips 94 off of or spaced away from the user's face, which may improve comfort. Because the flexible headgear 80 (in some embodiments) can automatically adjust to the shape and size of the user's head, the cheek pads 114 can also be automatically moved to suit the individual.

Figure 24:
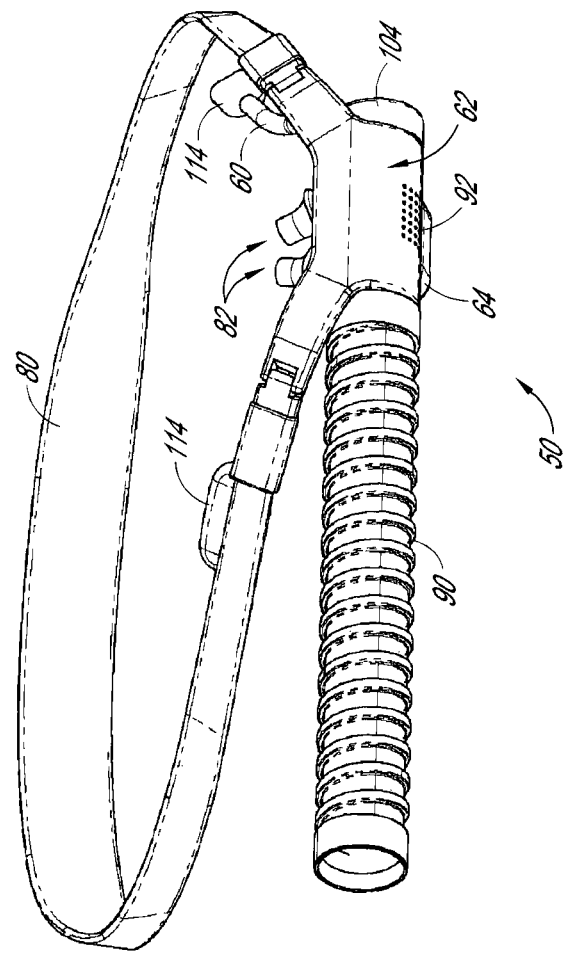
FIG. 24 is a front perspective view of another embodiment of a nasal interface.
Figure 25:
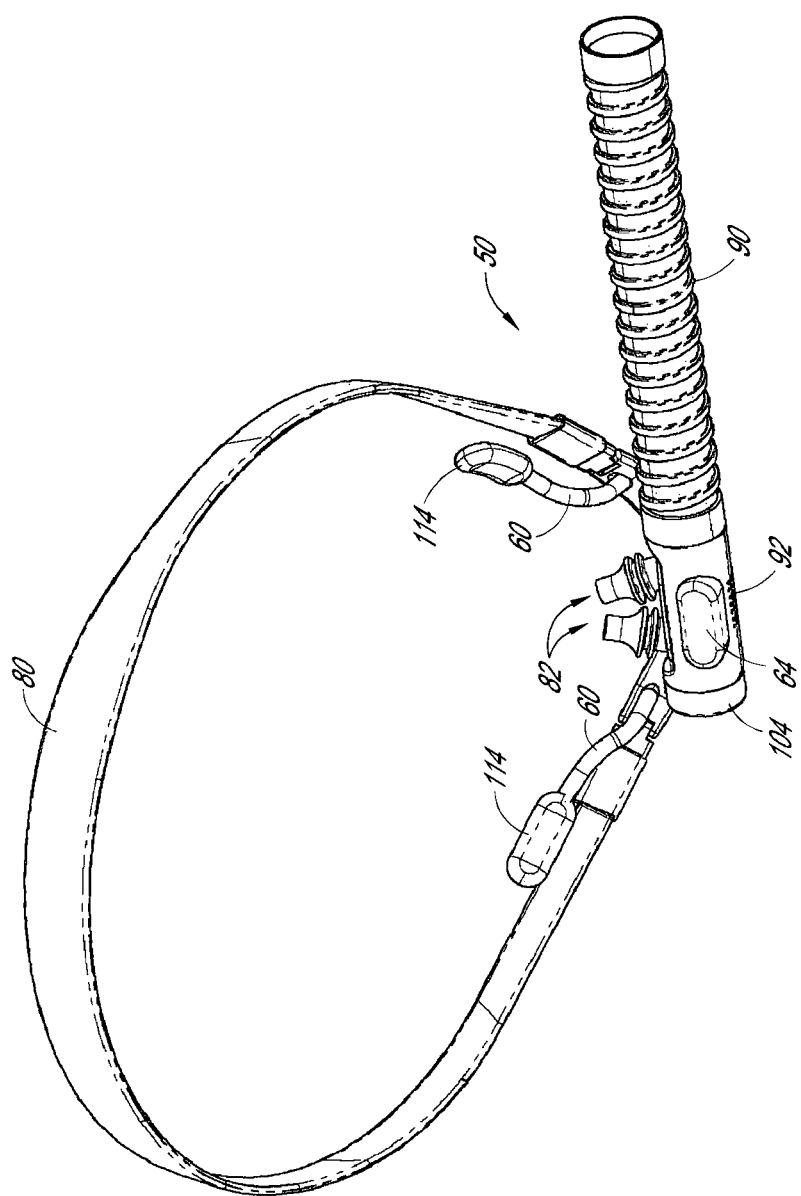
FIG. 25 is a rear perspective view of the nasal interface of FIG. 24.

FIGS. 24 and 25 illustrate a nasal interface 50 that is similar to the previously-described interfaces, in particular, those of FIGS. 8-15. However, the nasal interface 50 of FIGS. 24 and 25 locates the outlet 92 (e.g., exhaust vents/bias flow holes) on the frame 62 rather than locating it on the inner tube or manifold 104. The inner tube or manifold 104 preferably, however, has a hole or opening (not shown) that allows air or gas to pass through the manifold 104 to the bias holes of the outlet 92. Essentially, the interface 50 of FIGS. 24 and 25 reverses or switches the outlet 92 and the opening 112 of the arrangement of the interface 50 of FIGS. 8-15. Preferably, a sealed connection is provided between the inner tube or manifold 104 and the frame 62 to reduce or minimize unintentional leaks. The sealed connection can utilize seal members (e.g., O-rings) or simply a tight fit between the manifold 104 and the frame 62.

Figure 26:
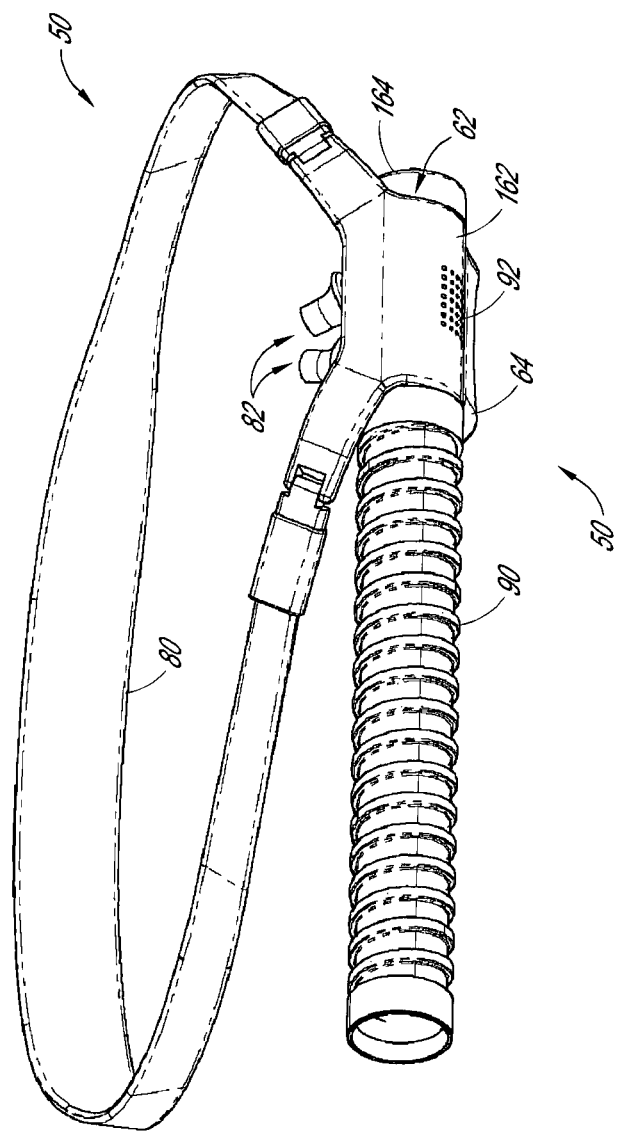
FIG. 26 is a front perspective view of another embodiment of a nasal interface.
Figure 27:
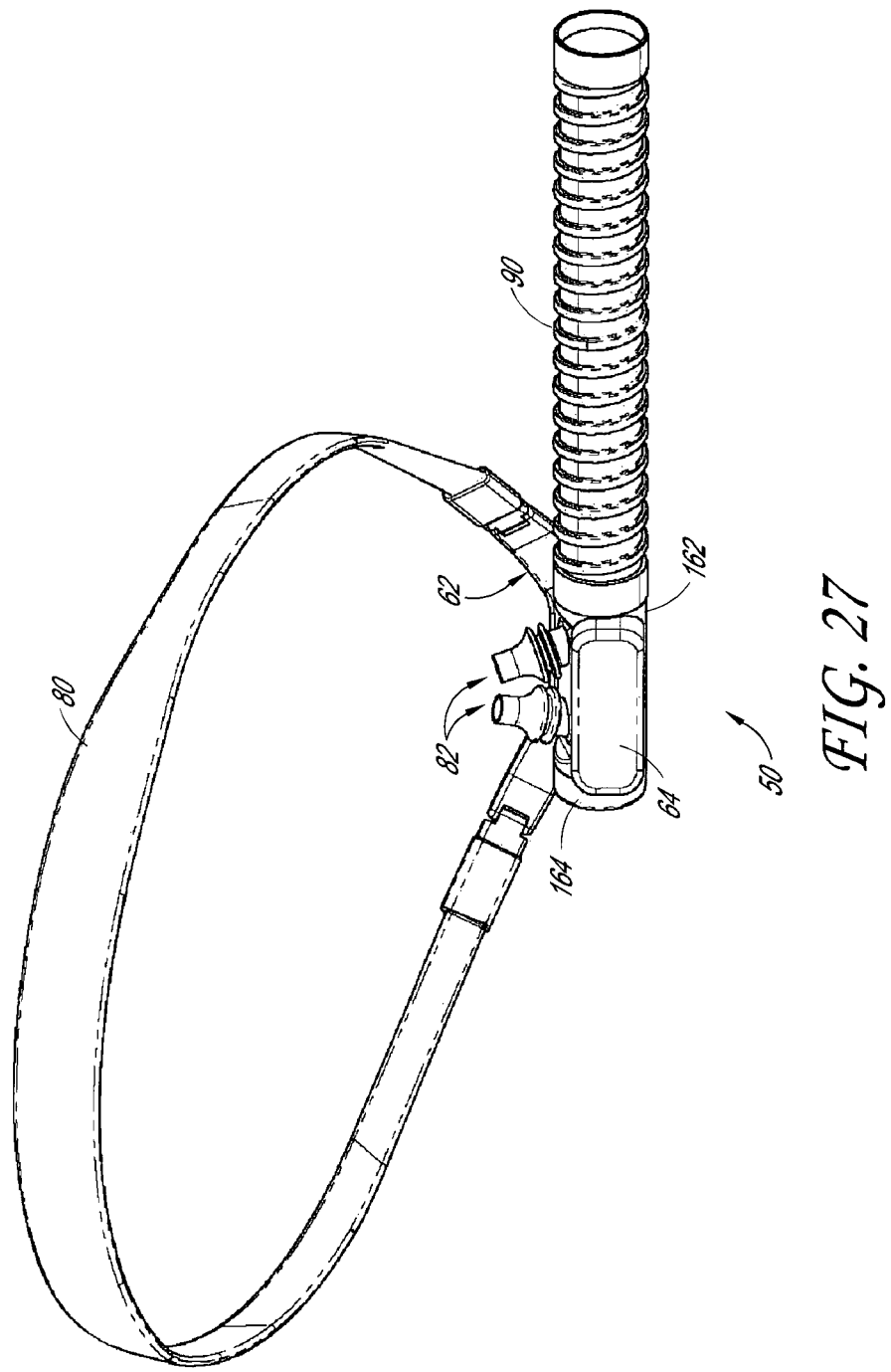
FIG. 27 is a rear perspective view of the nasal interface of FIG. 26.

FIGS. 26 and 27 illustrate a nasal interface 50 that is similar to the previously-described interfaces, in particular, those of FIGS. 8-15. However, the nasal interface 50 of FIGS. 26 and 27 locates the lip rest pad 64 and the nasal prong elements 82 on a generally hollow portion 162 (e.g., cylindrical or tubular portion) of the frame 62 that defines an interior chamber. The supply tube 90 can be secured to either end of the chamber defined by the hollow portion 162 and an end cap 164 can be provided to seal the opposing end. Alternatively, the supply tube 90 can include a cylindrical member configured to be received within the hollow portion 162 of the frame 62 and including an opening that permits fluid communication with the nasal prong elements 82. In addition, the interface 50 of FIGS. 26 and 27 omits the lateral arms of other interfaces 50. However, lateral arms similar to any of those described herein could be provided, if desired.

Figure 28:
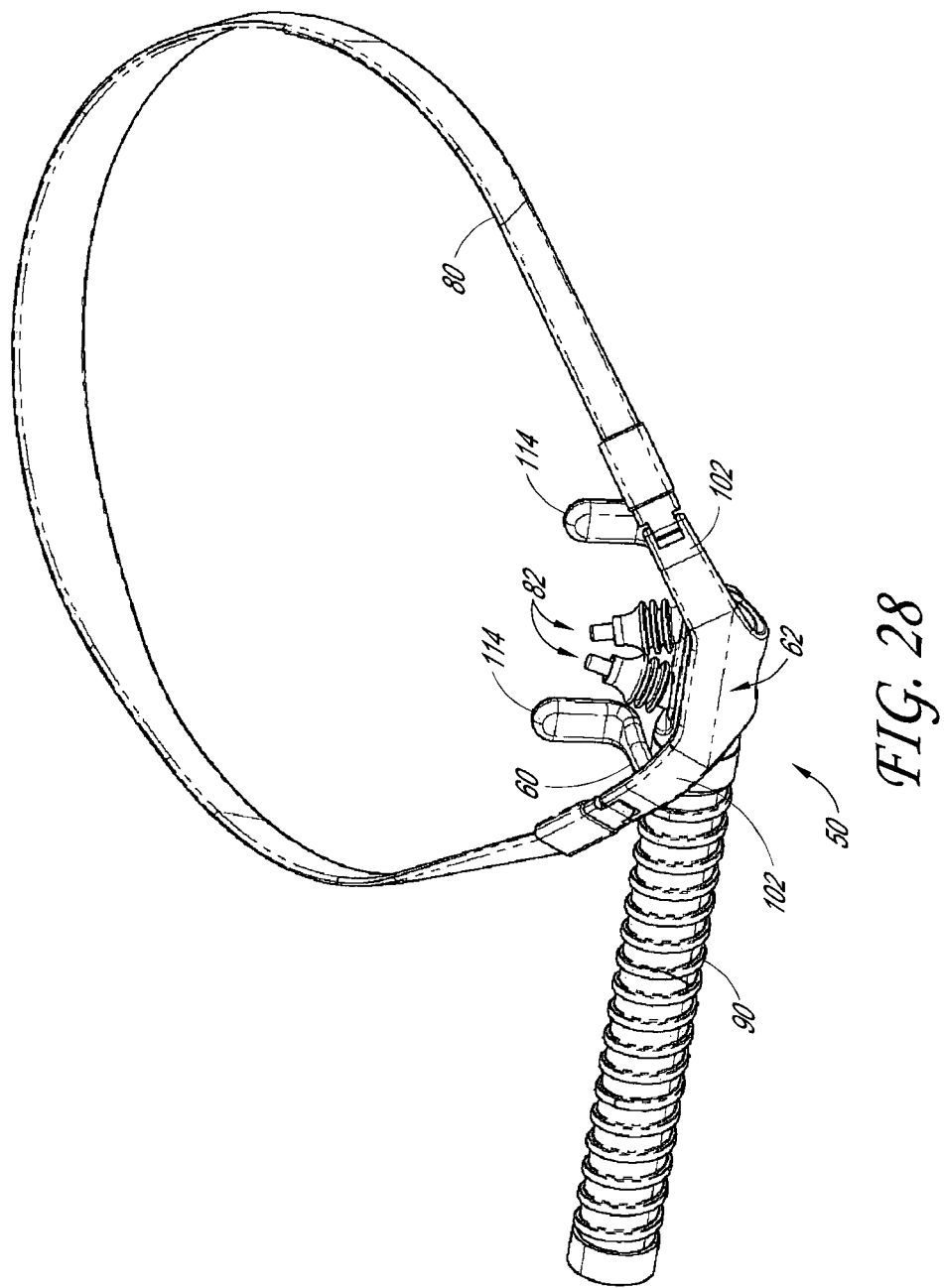
FIG. 28 is a front perspective view of another embodiment of a nasal interface.
Figure 29:
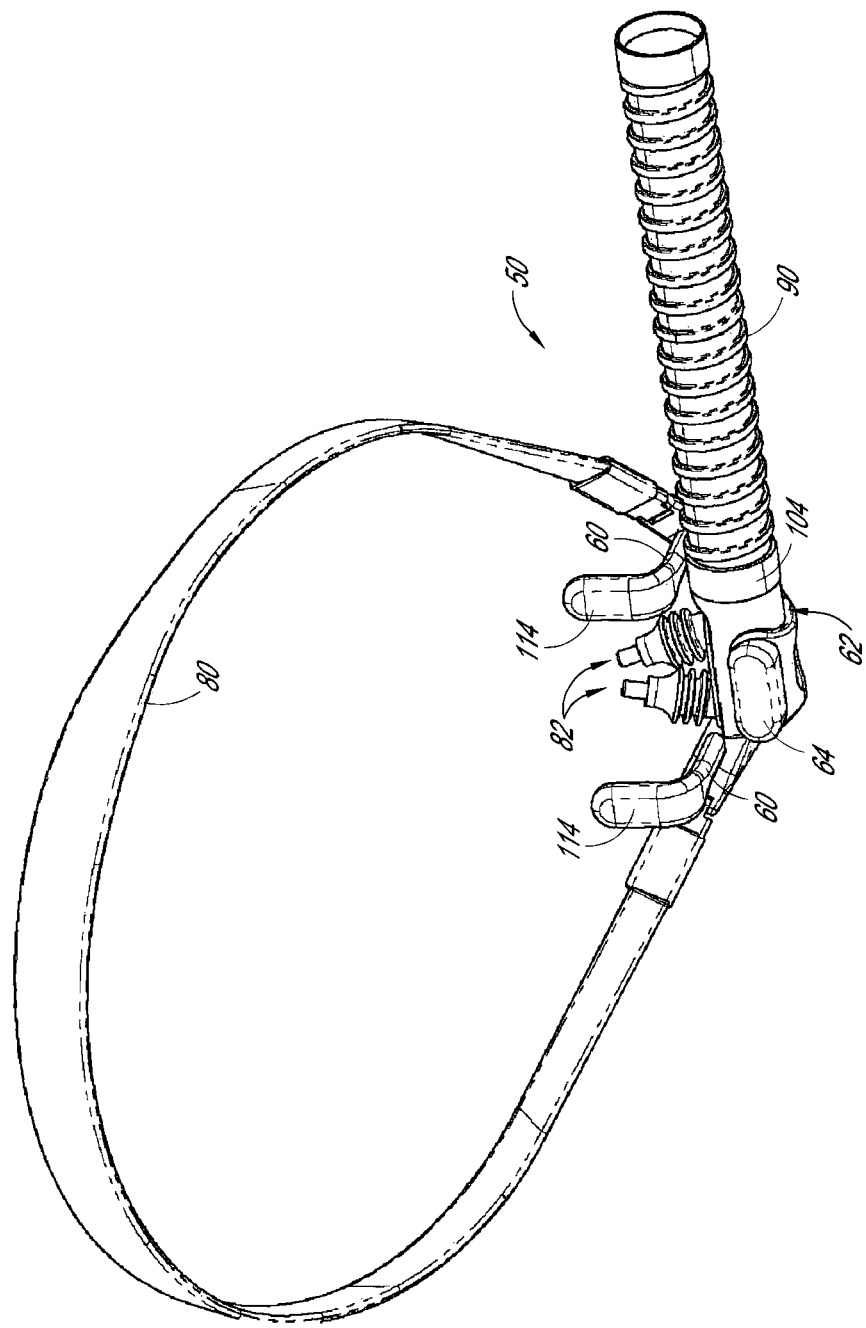
FIG. 29 is a rear perspective view of the nasal interface of FIG. 28.

FIGS. 28 and 29 illustrate a nasal interface 50 that is similar to the previously-described interfaces, in particular, those of FIGS. 8-15. However, the lateral arms 60 of the nasal interface 50 of FIGS. 28 and 29 have a narrower stance, or a narrower distance between them, compared to other interfaces 50 disclosed herein. The end portions or pads 114 of the lateral arms 60 preferably contact the user's face on each side of the nose, preferably on an inner portion of the cheek beside the lateral cartilage. The pads 114 can be positioned laterally inward of the zygomatic bones and next to the nasal flanks and/or directly below the eyes. The pads 114 can be substantially aligned with or near the end portions of the lateral side portions 102 of the frame 62. In some configurations, the pads 114 are located laterally inside of the end portions of the lateral side portions 102 of the frame 62. The lateral arms 60 can extend rearwardly from the frame 62 and then extend upwardly such that the lateral arms 60 have a generally L-shape when viewed from the side. Thus, the free ends or pads 114 can extend generally in a vertical direction having a greater vertical dimension than the horizontal dimension.

Figure 30:
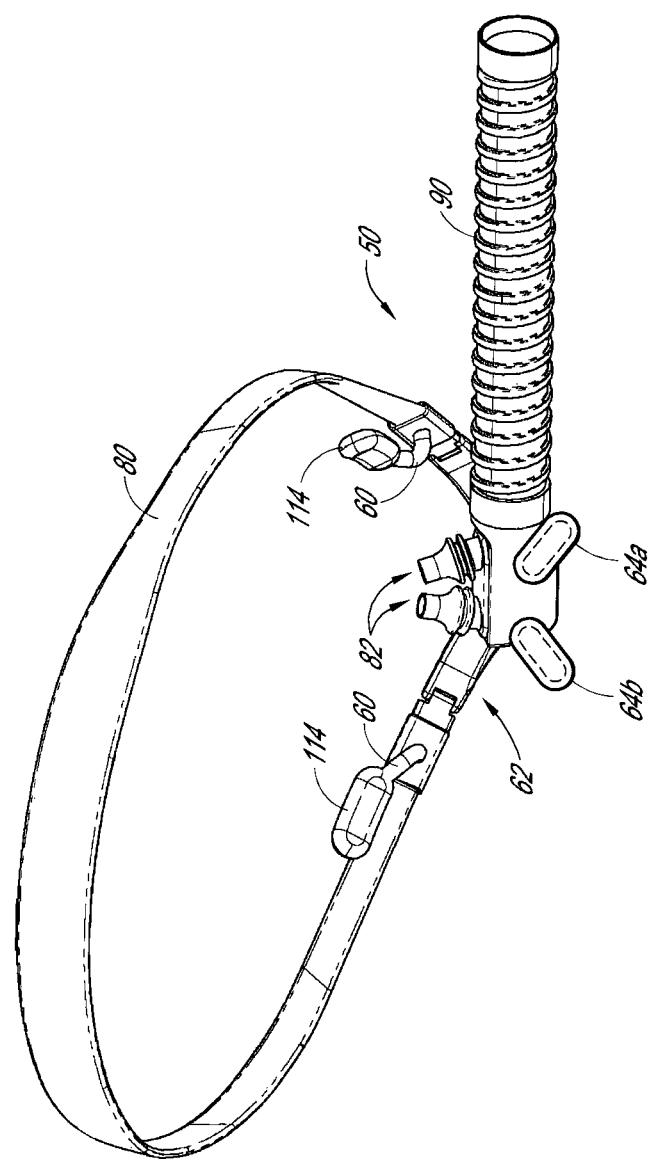
FIG. 30 is a rear perspective view of another embodiment of a nasal interface.

FIG. 30 illustrates a nasal interface 50 that is similar to the previously-described interfaces, in particular, those of FIG. 20 and FIG. 23. The illustrated nasal interface 50 of FIG. 30 is, in essence, a combination of the upper support arrangement (lateral arms 60 and pads 114) of the interface 50 of FIG. 23 and the lower support arrangement (support/pads 64a, 64b) of the interface of FIG. 20. Thus, preferably, there are two lower pads 64a, 64b that sit on the user's upper lip but towards the corners of the mouth. The pads 64a, 64b can be supported directly on the frame 62 or can be supported by an intermediate structure, similar to the arms 60 of the upper pads 114, for example. Other suitable arrangements can also be used. As described previously, such an arrangement can be beneficial in providing increased lateral stability and spreading load forces over a greater area. Having a single load point or area at the center of the upper lip can be uncomfortable to some users. Accordingly, distributing the load to the sides of the lip may improve comfort. Any combination of nasal delivery elements 82 and/or types of headgear 80 disclosed herein, or is otherwise suitable, can be used with the interface arrangement of FIG. 30.

Figure 31:
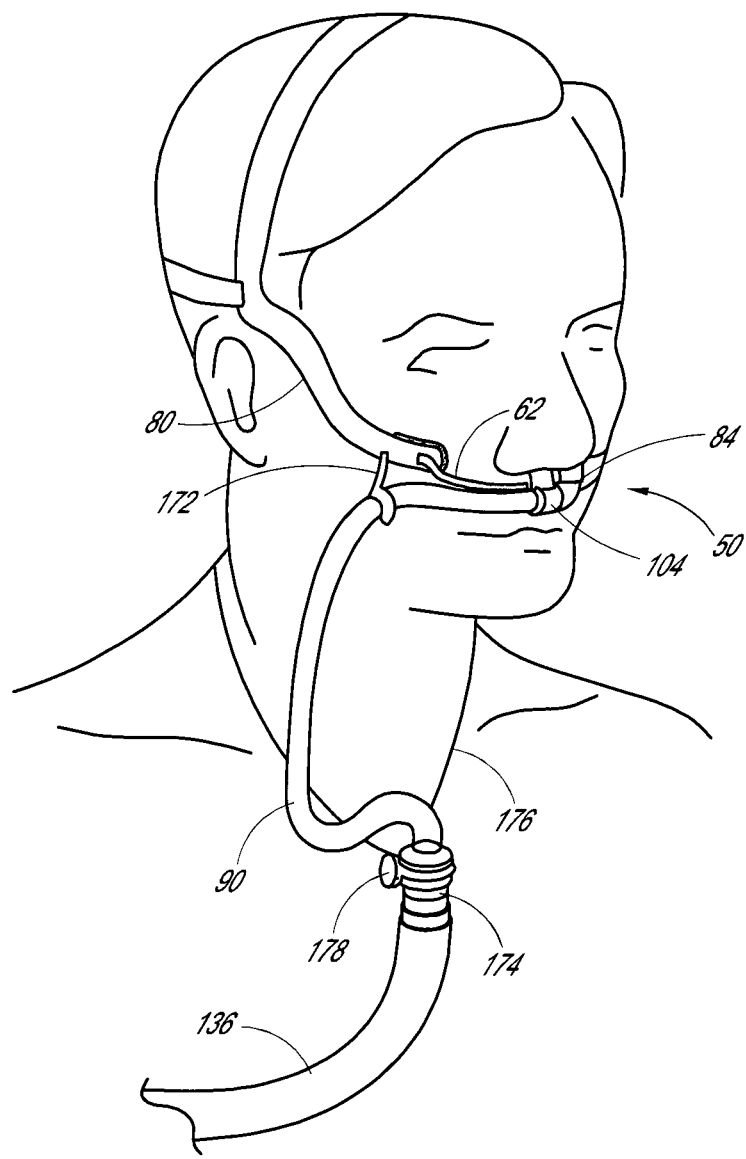
FIG. 31 is a front perspective view of another embodiment of a nasal interface positioned on a user.
Figure 32:
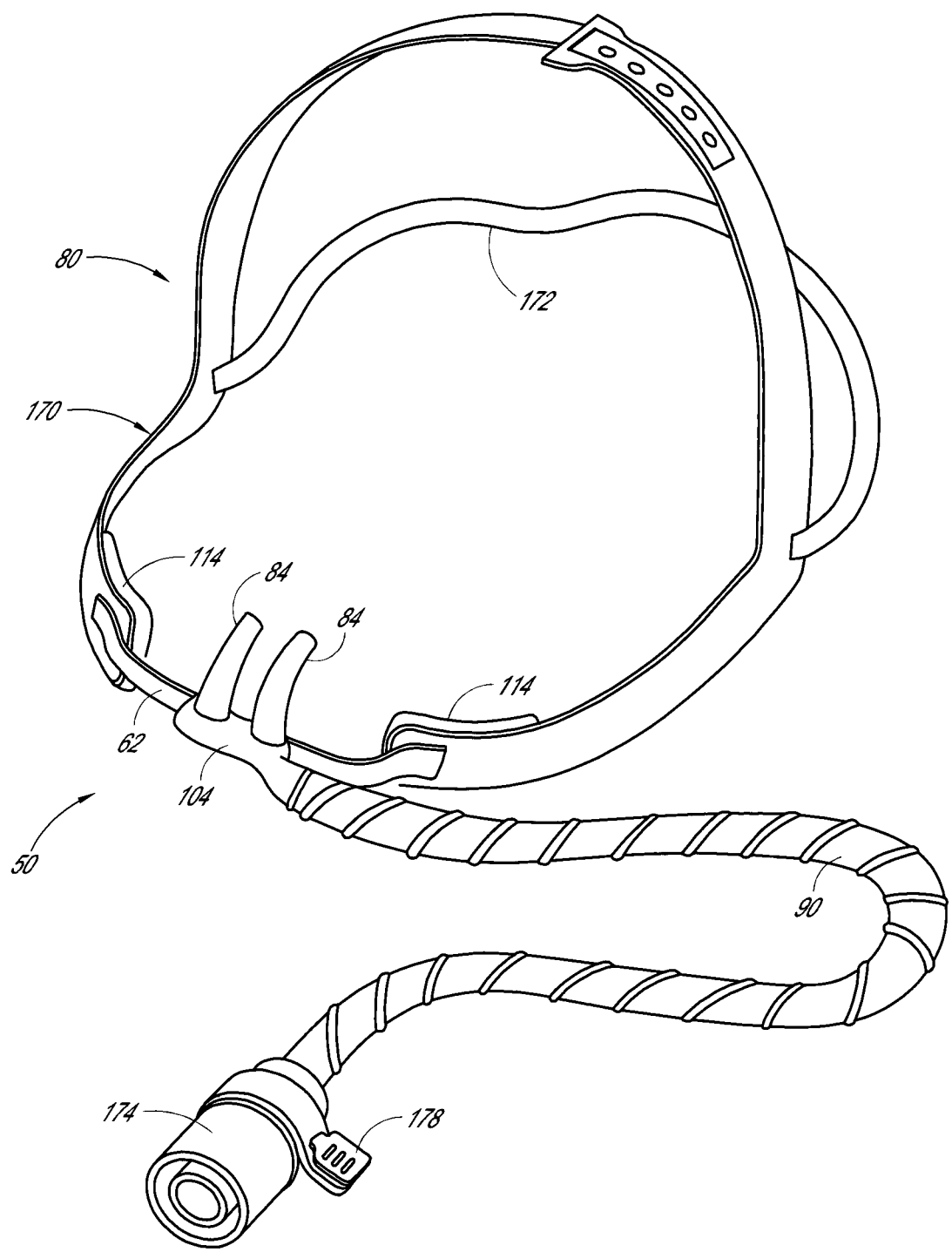
FIG. 32 is a front perspective view of the nasal interface of FIG. 31.

FIGS. 31 and 32 illustrate a nasal interface 50 that shares similarities to the previously-described interfaces. However, the nasal interface 50 of FIGS. 31 and 32 can comprise a cannula prong design having a pair of nasal prongs 84 supported by a body portion or manifold 104. The manifold 104 and prongs 84 preferably are supported off the lip of the user by a headgear 80 and frame 62, which may improve comfort by reducing or preventing a pressure point from forming on the lip and teeth of the user. Preferably, the cannula manifold 104 that supports the prongs 84 is low profile when viewed from above to reduce obstruction of expiratory flow from the nares and therefore reducing or minimizing the noise resulting from expiratory flow directed toward the cannula manifold 104. At least the front section of the headgear 80 can be a moulded, semi-rigid structure that is shaped to fit near or against the wearer's cheeks providing a stable structure for supporting the cannula portion (e.g., manifold 104 and prongs 84). The cannula portion can be attached to a semi-rigid bridge portion or frame 62, which extends between and is supported by the headgear 80 and preferably sits off of or spaced from the upper lip.

In some configurations, a front portion and top strap of the headgear 80 defines a semi-rigid headgear portion 170 that can be made from plastic and may include a soft lining or cushioning material on a portion or throughout at least an inner, user-contacting surface. The semi-rigid headgear portion 170 may include a baseball cap style of adjustment (e.g., releasable protrusions and openings) or any other known adjustment mechanism including hook-and-loop fastener, etc. The semi-rigid headgear portion 170 preferably maintains its shape when not fitted making it easy for the wearer to fit the cannula portion while positively locating the top and back straps in the right locations on the wearers head. When the top strap is correctly adjusted, preferably the design avoids any part of the headgear 80 coming into contact with the user's ears while positively maintaining the location of the cheek portions and cannula portion on the user's face. The headgear back strap 172 could be stretchable or could be a substantially non-stretch material with an adjustment mechanism included (not shown), such as those described above.

Each of the cheek support portions of the headgear 80 can include a cushioned pad 114 for comfort. The pads 114 may be made of a suitable soft material, such as a foam, gel or textile. In some arrangements, the pads 114 can be constructed from other suitable soft materials, such as a thermoplastic elastomer (TPE), silicone, or other similar materials. The pads 114 can be contoured to follow the shape of the user's cheeks. Preferably, the headgear 80 is sized and shaped or otherwise configured to position the pads 114 at a location similar to the pads 114 described in connection with the other embodiments herein. That is, for example, the pads 114 can rest in the general region of or near the zygomatic bones. In some configurations, the pads 114 can be located on or near the transition between the maxillary and zygomatic bones. In some configurations, the upper pads 114 are positioned laterally inward of the zygomatic bones and next to the nasal flanks and/or directly below the eyes. In some configurations, the pads 114 can be located at or near an inner portion of the cheek beside the lateral cartilage. Preferably, the pads 114 can be located on or near a line extending between a location just above the ear and a location below the nose.

The semi-rigid bridge portion or frame 62 can extend between the cheek pads 114 and can be made from any suitable material, such as plastic or metal. The use of a malleable metal or other formable material may allow the bridge 62 to be shaped to better fit each individual user. Preferably, at least some flexibility is provided by the bridge portion 62 so that when a user changes position (e.g. moves from lying on their back to lying on their side) the cannula prongs 84 (and/or pillows 86, if present) aren't pushed out of their nares or are less likely to be pushed out of their nares.

Preferably, any one or all of the headgear 80, the pads 114 and the frame 62 are configured to inhibit or prevent rocking of the nasal elements 82 (e.g., prongs 84). Thus, the headgear 80 and/or the frame 62 can be sufficiently stiff to inhibit or prevent significant twisting. Such resistance to twisting can be provided by features or properties of the headgear or frame 62 (e.g., material, thickness or height), by stiffening features (e.g., ribs, internal or external stiffening members) or by other suitable arrangements. Similarly, the pads 114 can be sufficiently tall or have a sufficient height to inhibit or prevent rocking of the nasal elements 82 (e.g., prongs 84). Similarly, this applies to the arrangements discussed below with respect to FIGS. 33-38.

The breathing tube or hose 90 is shown to have a side connection and may be reversible, as described above. However, the breathing tube or hose 90 could be a front connection incorporating an elbow, as previously described, for example, in connection with FIGS. 21 and 22. Optionally, a hose attachment clip 172 or other connection or support member can couple the tube 90 to the headgear 80/cheek pad 114 to transfer hose drag forces away from the cannula manifold 104 and prongs 84, thus reducing or minimizing the chances of the prongs 84 being dislodged from the user's nares. The supply tube 90 can include a connector 174, which permits coupling of the supply tube 90 to a supply tube or conduit 136. In some arrangements, a neck loop or strap 176 can be used to support a portion of the weight of the supply tube 136 and/or supply tube 90. An optional clip 178 can also or alternatively be provided, which permits clipping of the connector 174/tubes 90, 136 to the user's clothing or another object.

Figure 33:
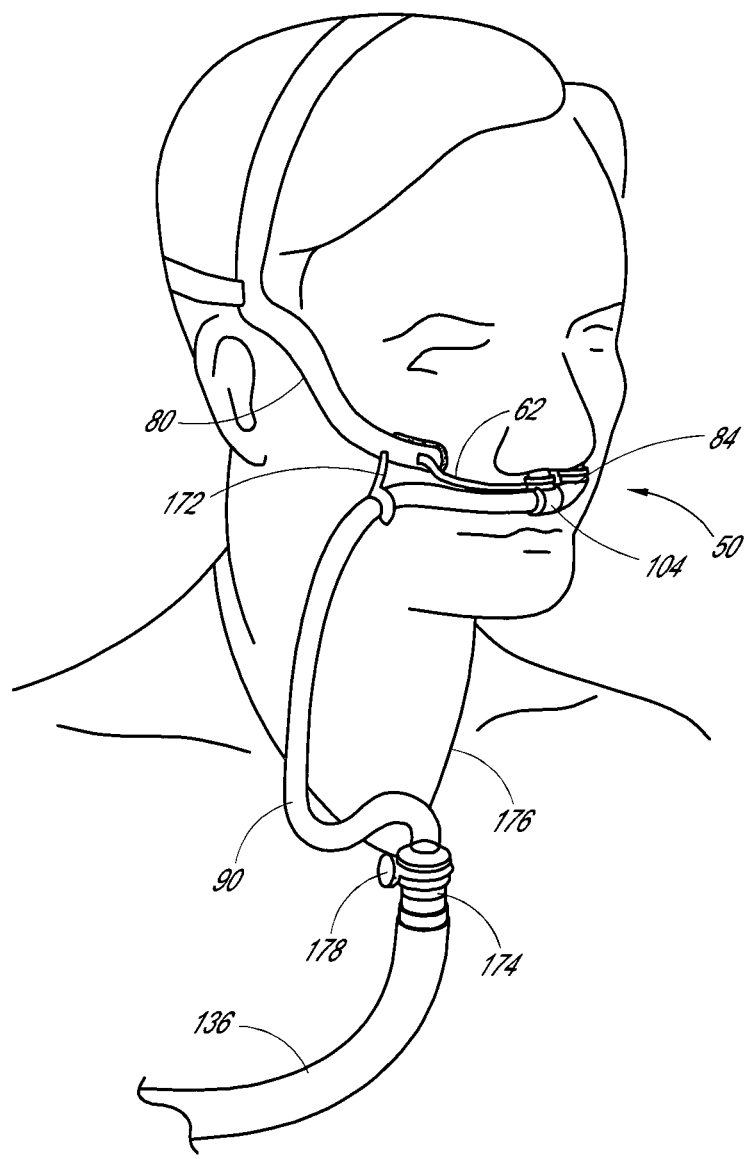
FIG. 33 is a front perspective view of another embodiment of a nasal interface positioned on a user.
Figure 34:
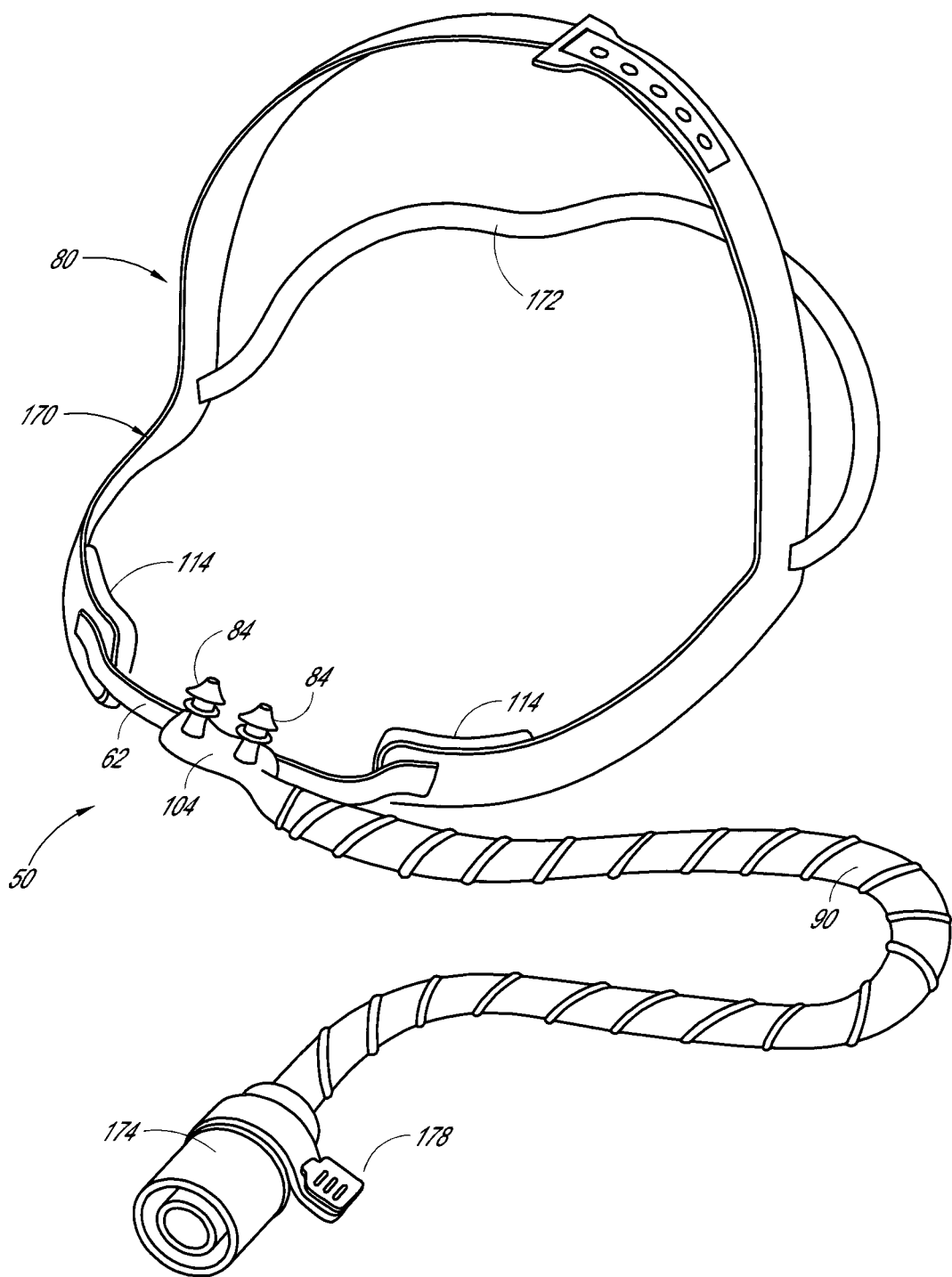
FIG. 34 is a front perspective view of the nasal interface of FIG. 33.

FIGS. 33 and 34 illustrate a nasal interface 50 that is similar to the previously-described interfaces, in particular, that of FIGS. 31 and 32. However, the nasal interface 50 of FIGS. 33 and 34 includes nasal pillows 86 instead of traditional cannula prongs (84 in FIGS. 31 and 32. Such an arrangement allows for the incorporation of a controlled bias flow system including a bias flow outlet (holes) 92 (not shown), such as any of those previously described. In some arrangements, the interface 50 can include a prong 84/pillow 86 combination, such as those shown in FIGS. 7a-7c and 17-20, for example. Preferably, with such an arrangement, a base of the nasal pillows 86 are positively located relative to the user's nares while the support structure (e.g., manifold 104) for the prongs 84 and/or pillows 86 remains clear of the user's lip and nose.

Figure 35:
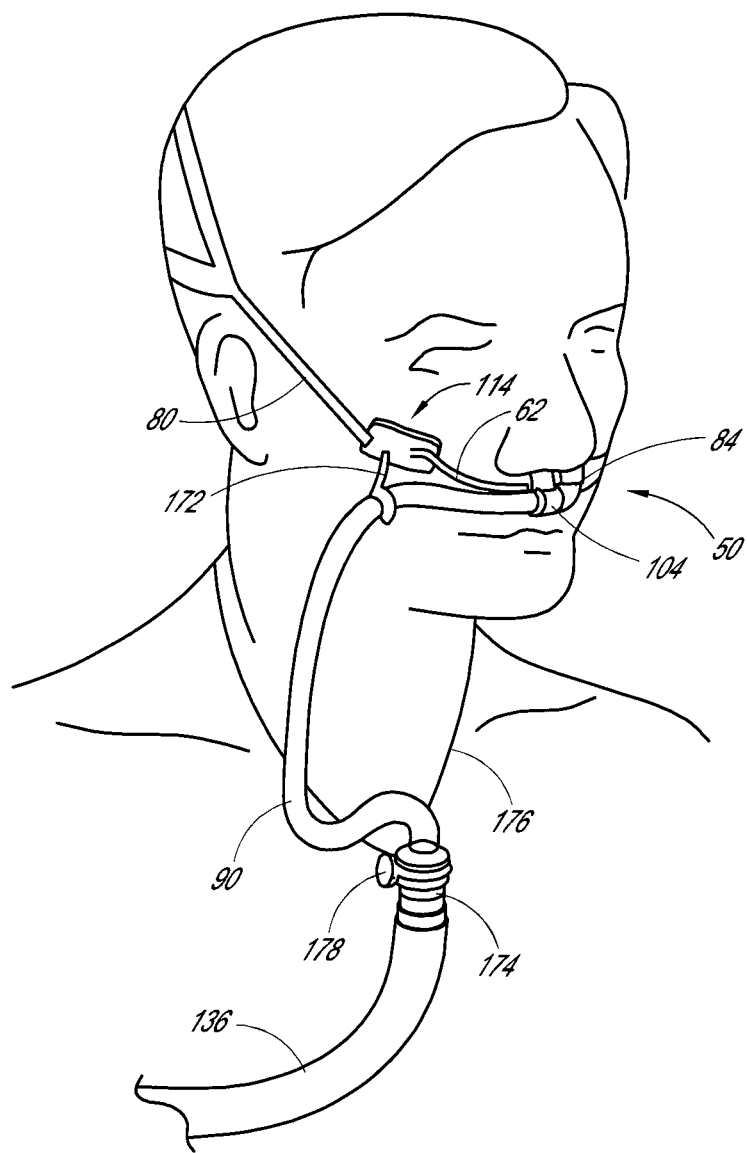
FIG. 35 is a front perspective view of another embodiment of a nasal interface positioned on a user.
Figure 36:
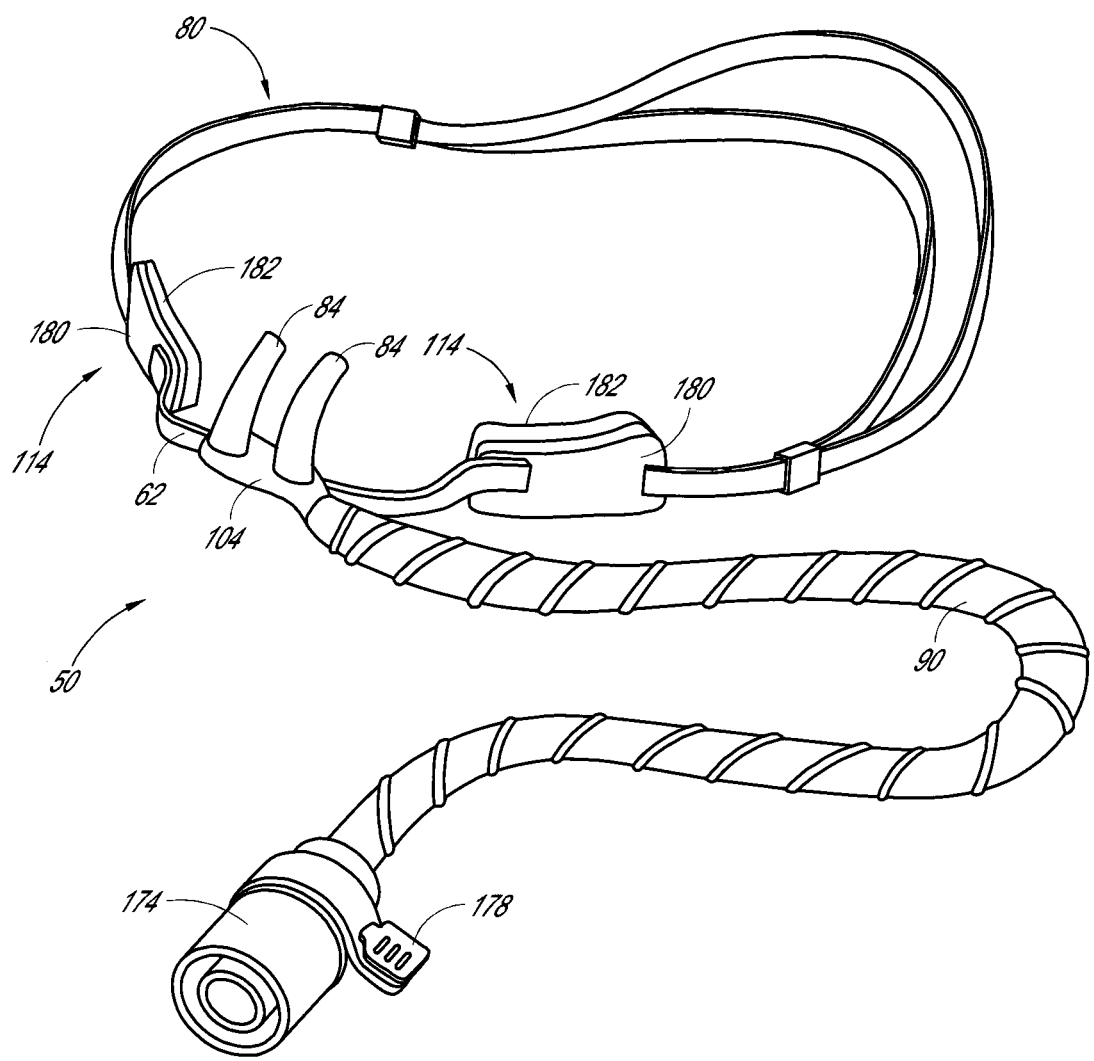
FIG. 36 is a front perspective view of the nasal interface of FIG. 35.

FIGS. 35 and 36 illustrate a nasal interface 50 that is similar to the previously-described interfaces, in particular, those of FIGS. 31-34. However, the nasal interface 50 of FIGS. 35 and 36 includes a traditional cannula prong design (e.g., incorporating nasal prongs 84 extending from a manifold 104) that preferably is supported off of the user's lip by a semi-rigid bridge portion 62. Preferably, the cannula manifold 104 that supports the prongs 84 is low profile when viewed from above to reduce obstruction of expiratory flow from the nares and therefore reducing or minimizing the noise resulting from expiratory flow directed toward the cannula manifold 104. In the illustrated configuration, the semi-rigid bridge portion or frame 62 extends between and preferably is attached to cheek support pads 114. The cheek support pads 114 can include a base portion 180 and a pad portion 182. The headgear 80 can be attached to each of the cheek support pads 114 (e.g., the base portion 180) by any suitable arrangement. Moreover, headgear 80 can be of any suitable arrangement, including any of those disclosed herein. In the illustrated configuration, the cheek pads 114, bridge 62 and cannula assembly (e.g., prongs 84 and manifold 104) are held to the user's head with a soft or stretch or non-stretch headgear arrangement, which can include an adjustment mechanism (not shown).

As described previously, each of the cheek support portions or cheek pad units 114 of the headgear 80 can include a cushioned pad 182 for comfort. The pads 182 may be made of a suitable soft material, such as a foam, gel or textile. In some arrangements, the pads 182 can be constructed from other suitable soft materials, such as a thermoplastic elastomer (TPE), silicone, or other similar materials. The pads 182 can be contoured to follow the shape of the user's cheeks. Preferably, the headgear 80 is sized and shaped or otherwise configured to position the pads 182 at a location similar to the pads 114 described in connection with the other embodiments herein.

The semi-rigid bridge portion or frame 62 can extend between the cheek pad units 114 and can be made from any suitable material, such as plastic or metal. The use of a malleable metal or other formable material may allow the bridge 62 to be shaped to better fit each individual user. Preferably, at least some flexibility is provided by the bridge portion 62 so that when a user changes position (e.g. moves from lying on their back to lying on their side) the cannula prongs 84 (and/or pillows 86, if present) aren't pushed out of their nares or are less likely to be pushed out of their nares.

The breathing tube or hose 90 is shown to have a side connection and may be reversible, as described above. However, the breathing tube or hose 90 could be a front connection incorporating an elbow, as previously described, for example, in connection with FIGS. 21 and 22. Optionally, a hose attachment clip 172 or other connection or support member can couple the tube 90 to the headgear 80/cheek pad units 114 to transfer hose drag forces away from the cannula manifold 104 and prongs 84, thus reducing or minimizing the chances of the prongs 84 being dislodged from the user's nares. Such an arrangement may be more effective if the headgear 80 is substantially non-stretchable or has only a limited stretchable section so that hose drag does not pull the whole cheek pad unit 114/cannula assembly (e.g., manifold 104 and prongs 84) away from the user's face. The supply tube 90 can include a connector 174, which permits coupling of the supply tube 90 to a supply tube or conduit 136. In some arrangements, a neck loop or strap 176 can be used to support a portion of the weight of the supply tube 136 and/or supply tube 90. An optional clip 178 can also or alternatively be provided, which permits clipping of the connector 174/tubes 90, 136 to the user's clothing or another object.

Figure 37:
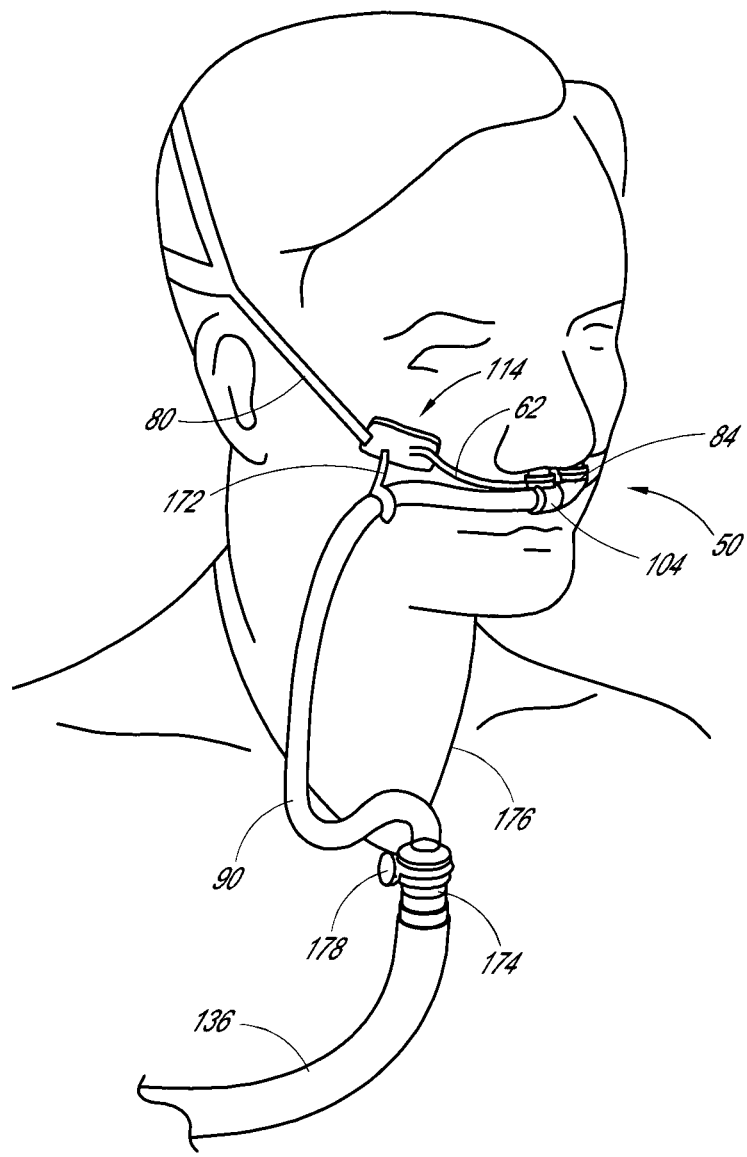
FIG. 37 is a front perspective view of another embodiment of a nasal interface positioned on a user.
Figure 38:
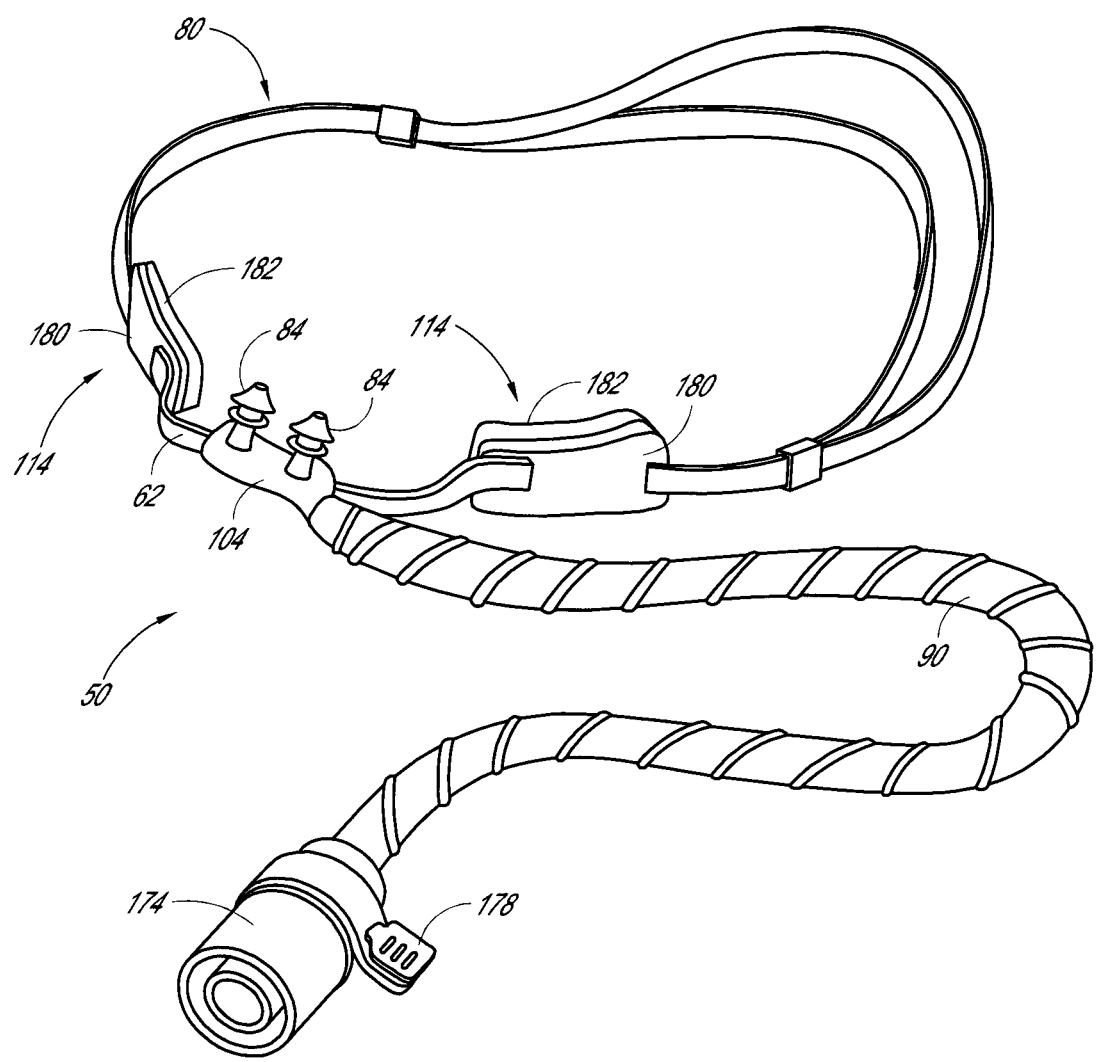
FIG. 38 is a front perspective view of the nasal interface of FIG. 37.

FIGS. 37 and 38 illustrate a nasal interface 50 that is similar to the previously-described interfaces, in particular, those of FIGS. 35 and 36. However, the nasal interface 50 of FIGS. 37 and 38 includes nasal pillows 86 instead of traditional cannula prongs (84 in FIGS. 35 and 36). Such an arrangement allows for the incorporation of a controlled bias flow system including a bias flow outlet (holes) 92 (not shown), such as any of those previously described. In some arrangements, the interface 50 can include a prong 84/pillow 86 combination, such as those shown in FIGS. 7a-7c and 17-20, for example. In some arrangements, the interface 50 can include a prong 84/pillow 86 combination, such as those shown in FIGS. 7a-7c and 17-20, for example. Preferably, with such an arrangement, a base of each of the nasal pillows 86 is positively located relative to the user's nares while the support structure (e.g., manifold 104) for the prongs 84 and/or pillows 86 remains clear of the user's lip and nose. Preferably, the interface 50 of FIGS. 37 and 38 incorporates a strap headgear 80, which can be adjustable or stretchable, instead of a semi-rigid headgear as described previously in connection with other embodiments.

Figure 39:
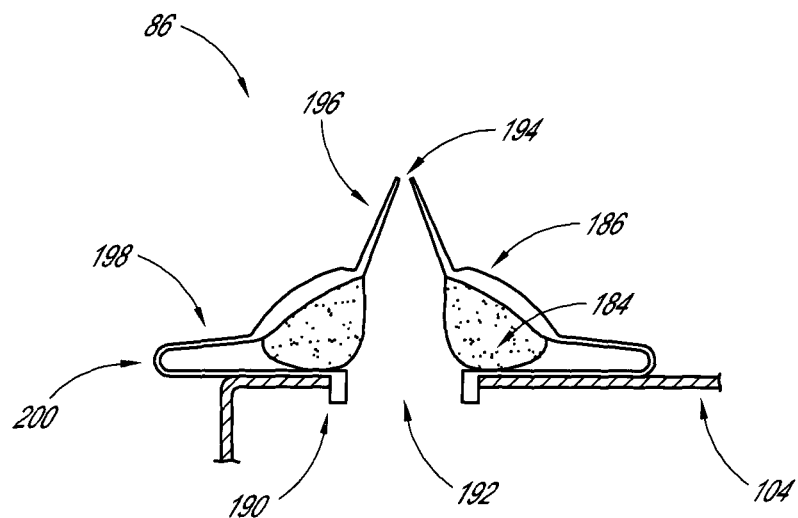
FIG. 39 is a sectional view of a nasal element in a first position.
Figure 40:
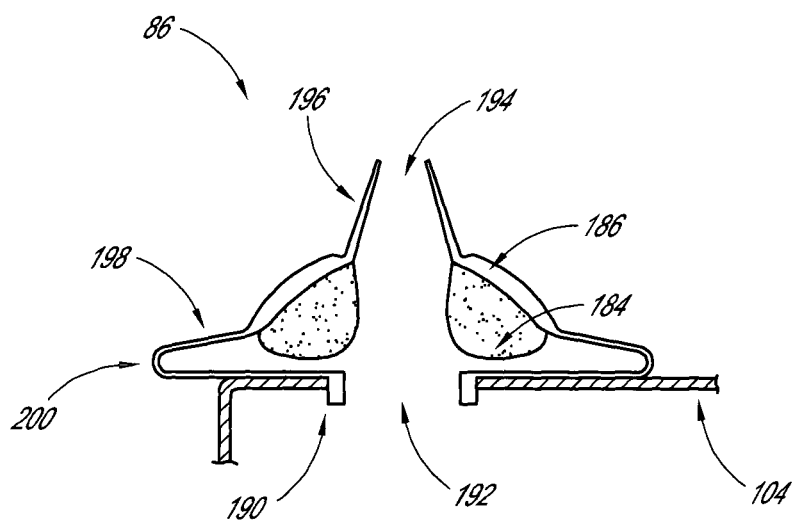
FIG. 40 is a section view of the nasal element of FIG. 39 in a second position.

FIGS. 39 and 40 illustrate an embodiment of a nasal delivery element 82 that can be used with any of the interfaces 50 described herein. The nasal delivery element 82 of FIGS. 29 and 40 is especially well-suited for use with the interfaces 50 of FIGS. 33 and 34 and FIGS. 37 and 38. In those or other interfaces 50, the support structure (e.g., manifold 104) could be provided with nasal pillows 86 that inflate (e.g., are coupled to the supplied flow of breathing gas) toward the user's nares applying increased sealing pressure as the delivered pressure increases. In order to provide sufficient sealing at low pressure, each pillow 86 can include inner soft and deformable support structures 184 located inside the pillow 86.

FIG. 39 shows a pillow 86 at low delivery pressure, such as about 4 cm H2O, for example and without limitation. Preferably, the pillow 86 has a thickened upper nare locating portion or dome 186 that, in use, rests against the user's nare and is supported from below by the deformable support structure 184, which can be a foam, gel or ribbed (e.g., concertina/bellows) structure among other possible deformable materials/structures. Preferably, the deformable support structure 184 is formed into a ring or is annular in shape and is attached to the underside of the dome 186. Thus, preferably, the deformable support structure 184 and the thickened locating dome 186 surround the opening or internal passage of the pillow 86. The deformable support structure 184 can position the upper end of the pillow 86 at a desired minimum distance from the manifold 104 when the pillow 86 is not pressurized or is at low pressure to inhibit or prevent excessive collapse of the pillow 86.

The deformable support structure or support ring 184 can be configured to provide a leak path between the lower surface of the support ring 184 and the surface of the pillow 86 structure that is adjacent to the manifold 104 upon which the support ring 184 rests. This leak path will allow air to pass into the rolling portion of the pillow 86 thus increasing the pressure in that region as the CPAP pressure is increased and causing the upper surfaces (e.g., dome 186 and a prong portion 196) of the pillow 86 to extend upwards towards the orientation of FIG. 40. The leak path can be formed via an uneven or ribbed lower surface on the support ring 184, via holes through the support ring 184 or via any other method that allows air flow from an inlet or entry 192 to the outer periphery of the pillow 86. Other arrangements are also possible, such as providing the bottom of the support ring 184 with an angled or tapered surface facing the inlet or entry 192 such that the incoming gas acting on the angled or tapered surface creates a force acting on the support ring 184 having an axial component to provide the initial lifting of the support ring 184 and access to the outer periphery of the pillow 86.

FIG. 40 shows the pillow 86 at a higher delivery pressure, such as greater than or equal to 10 cm H2O, for example and without limitation. The pillow 86 preferably includes an annular base 190 that defines a relatively wide, low-restriction inlet or low-restriction gas entry 192 from the support manifold 104 (or other support structure) and a relatively narrow, higher-restriction outlet or higher-restriction gas exit 194 at the tip of a tube portion or prong portion 196 of the pillow 86, which extends upwardly or axially away from the locating dome 186. The gas entry 192 preferably has a greater diameter or cross-sectional area than the gas exit 194 such that pressure can build up within the pillow 86. In some configurations, the gas entry 192 can have a greater diameter or cross-sectional area than any portion of the tube or prong portion 196 of the pillow 86 or any other portion above (in FIGS. 39 and 40) or downstream of the locating dome 186.

In the illustrated arrangement, a thin-walled portion 198 extends between and preferably connects the base 190 to the locating dome 186. At higher delivery pressures, the restriction caused by the restriction gas exit 194 (relative to the gas entry 192) induces enough positive pressure inside the pillow 86 to increase the volume of the pillow 86 (and/or elongate/longitudinally extend the pillow 86) by forcing the locating dome 186 toward the nare of the user resulting in increased sealing force on the nare and, therefore, preferably increased contact surface area on the nare as the soft tissue compresses. The relatively rigid locating dome 186 and thin section or thin-walled portion 198 of the pillow 86 work together to longitudinally extend the pillow 86 and direct force toward the nare as the internal pressure increases. Thus, the pillow 86 can vary in length along with variations in internal pressure, at least in the absence of external forces sufficient to inhibit or prevent such elongation or longitudinal extension. In use, under some conditions, the pillow 86 may simply increase a sealing pressure rather than undergoing elongation or substantial elongation.

The thin-walled portion 198 can define a hinge point, roll point, roll section or rolling hinge 200 (collectively referred to herein for convenience as a "roll point") that may be a single 180 degree roll as shown in FIGS. 39 and 40 or may include multiple rolls in a bellows structure in order to reduce the overall diameter of the lower portion or base portion of the pillow 86. The roll point 200 provides the added advantage of allowing the pillows 86 to move horizontally relative to one another at least to some degree to accommodate the range of spacing of nares associated with different users. As described previously, the pillow 86 and manifold 104 may be formed as one component or as a unitary structure out of any suitable material (e.g., silicon) with the manifold portion 104 having a thicker wall section to achieve the desired rigidity. Alternatively, the pillow(s) 86 and manifold 104 can be separate components made from the same or different materials, similar to other arrangements disclosed herein. The deformable support structure 184 can be affixed to the locating dome 186 by any suitable arrangement, such as using an adhesive, for example.

A semi-rigid and substantially non-stretch headgear arrangement 80, such as that described in connection with FIGS. 31-34, can be especially advantageous for use in combination with the extending pillows 86 of FIGS. 39 and 40. Such a semi-rigid and substantially non-stretch headgear arrangement 80 provides a limiter to movement of the frame 62 (or other structure supporting the pillows 86) that forces expansion in a direction towards the user's face rather than allowing the supporting structure to move away from the user's face. Such a non-stretch or rigid headgear 80 creates a fixed (but preferably adjustable) circumference for the loop around the user's head created by the interface 50 and headgear 80. Having a fixed circumference loop means that when the pillows 86 expand under pressure, the expansion will be directed towards the face of the user, as the headgear 80 will not allow for any significant expansion of the loop. Having the pillows 86 extend towards the face will increase the contact with the user's nares and improve the seal, especially at higher pressures.

A flexible non-stretch strap/headgear arrangement 80 (e.g., the headgear 80 of FIGS. 35-38) can also direct the prong expansion towards the user's face, but may provide less rotational stability. As a result, desirable positioning of the pads (e.g., 64, 114) on the face may become more important with such an arrangement. A rigid headgear arrangement that extends from the nose, over the temple and over the crown of the user's head is beneficial as it applies forces through the pillows 86 of the interface 50 in a direction generally or substantially perpendicular to the lower surfaces of the user's nose. Being rigid inhibits or prevents rotation of the interface 50 due to twisting of headgear straps and reduces or minimizes the chances of the pillows 86 being dislodged from user's nares. Advantageously, keeping the rigid part of the headgear 80 away from the rear of the user's head can help with comfort as it reduces the likelihood of any sharp or hard edges digging into the head when the user's head resting on a sleep pillow.

Figure 41:
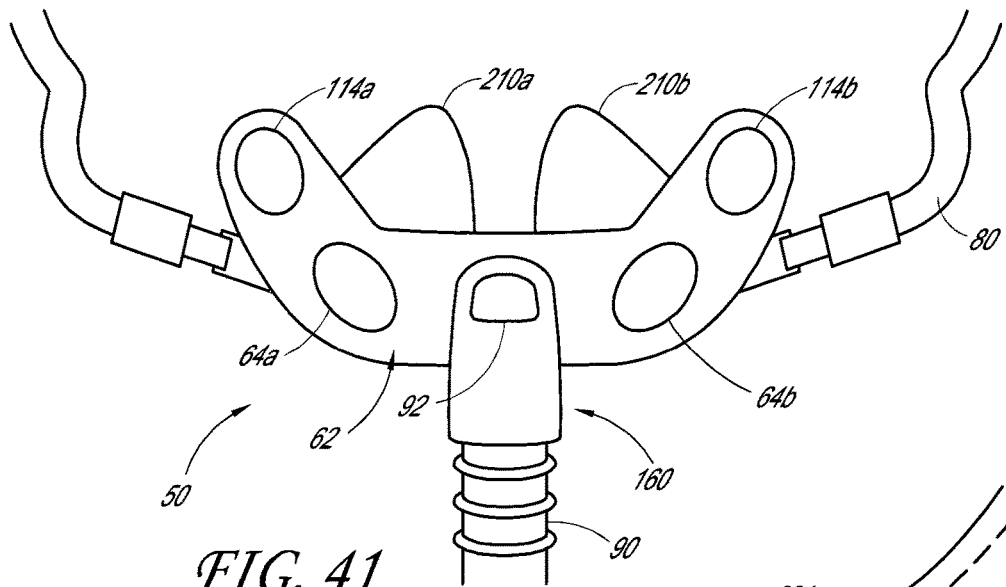
FIG. 41 is a front perspective view of another embodiment of a nasal interface.
Figure 44:
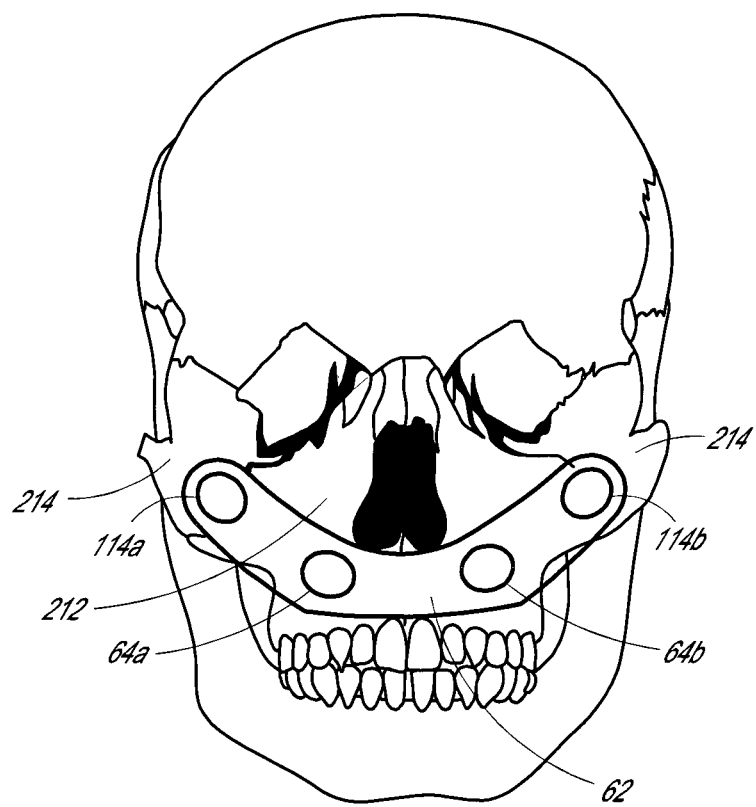
FIG. 44 is a front view of a support or frame portion of the nasal interface of FIG. 41 overlaid on a human skull illustrating a desired positioning relative to the bones of the skull.

FIGS. 41 through 44 illustrate a nasal interface 50 that is similar to the previously-described interfaces, in particular, those of FIGS. 19, 20 and 41. Preferably, the nasal interface 50 of FIGS. 41 through 44 includes a semi-rigid or rigid frame 62 with multiple stabilizing pads. For example, the interface 50 can include four stabilizing pads 114a, 114b, 64a, 64b. In the illustrated arrangement, the interface 50 includes two optional lateral stabilizer cushions 210a, 210b. The illustrated interface 50 also includes flexible nasal pillows 86. Preferably, the four stabilizing pads 114a, 114b, 64a, 64b are symmetrically positioned on either side of the face. With reference to FIG. 44, the two lower pads 64a, 64b preferably are positioned on the lower maxilla 212. The two upper pads 114a, 114b preferably are located on or near the transition between the maxillary 212 and zygomatic 214 bones. The stabilizing pads 114a, 114b, 64a, 64b are intended to provide contact points or areas with the face that inhibit, reduce or prevent rocking of the frame 62 and/or interface 50 in an up and down direction. In other arrangements, the upper pads 114a, 114b can be located positioned laterally inward of the zygomatic bones 214 and next to the nasal flanks and/or directly below the eyes. In some configurations, the pads 114a, 114b can be located at or near an inner portion of the cheek beside the lateral cartilage. The pads 114a, 114b, 64a, 64b can be made from a soft cushioning material such as foam, gel, fabric, thermoplastic elastomer (TPE), silicone, or other similar materials so as to be comfortable on the user's face.

Figure 42:
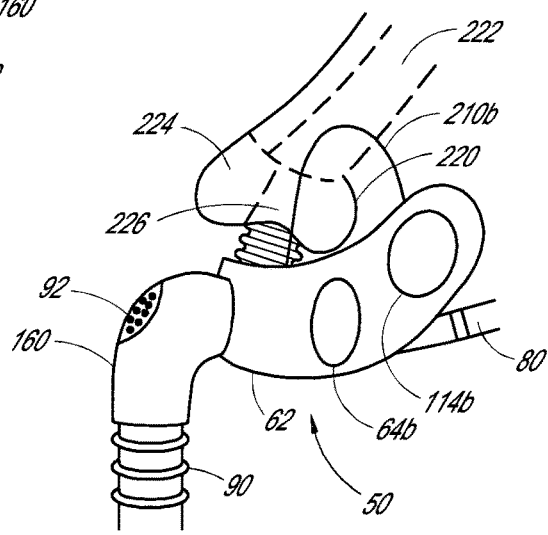
FIG. 42 is a side view of the nasal interface of FIG. 41 positioned on a user.
Figure 43:
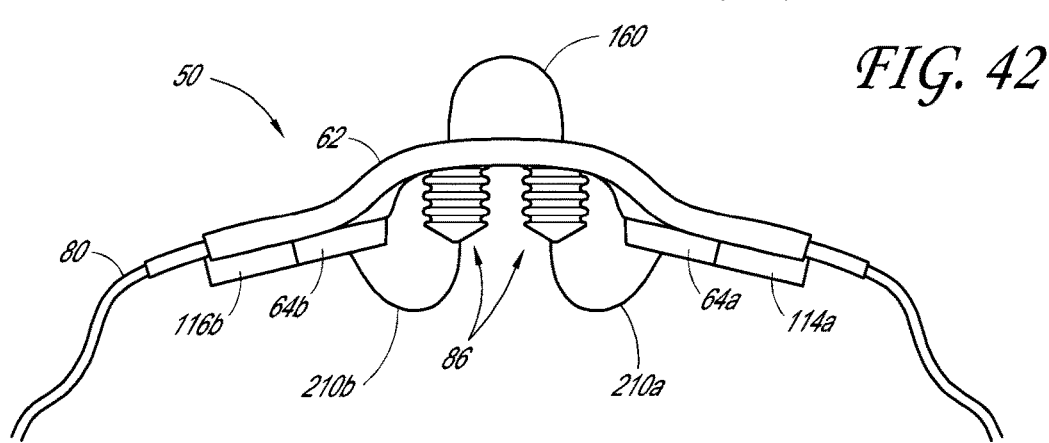
FIG. 43 is a top view of the nasal interface of FIG. 41.

With reference to FIG. 42, the lateral stabilizing cushions 210a, 210b preferably are positioned so that they extend over the alar grooves 220 and the upper lateral cartilage or lateral nose 222. Preferably, the cushions 210a, 210b are located low on the lateral nose 222 and configured to avoid significant collapsing of the nasal flanks. Thus, (when viewed from the side) a forward edge of each stabilizing cushion 210a, 210b is positioned forward of a portion or an entirety of the alar groove 220 and can be positioned rearward of the tip of the nose 224 extending through the ala or alar sidewalls 226 of the nose. Moreover, a rearward edge of each stabilizing cushion 210a, 210b can be positioned rearward of a portion or an entirety of the alar groove 220. In some configurations, the stabilizing cushions 210a, 210b extend upwardly from the frame 62 from a location below, near or at a lower end of the alar groove 220 or alar sidewall 226 to an upper edge or uppermost point that is above the rearward or upper end of the alar groove 220 and/or the alar sidewall 226 and located within the lateral nose 222. Preferably, the stabilizing cushions 210a, 210b provide additional rotational and/or lateral stability to the interface 50 by filling the gap between the nose and the mask frame 62. These cushions 210a, 210b can be made from a soft deformable material such as foam, the density of which will not be sufficient to squeeze the nasal passages shut. These could also be air filled balloon-like structures, which can be pre-filled (during manufacture) or filled via the source of breathing gas. In some configurations, reinforcement members, stiffening members or rigid supports (not shown) can be provided to add support or maintain a shape of the cushions 210a, 210b. Such members or supports can extend in an upward direction from the frame 62. In some configurations, the members or supports can extend along an edge of the cushions 210a, 210b, such as on the body of the cushion 210a, 210b just inward of the edge. Such stabilizing cushions 210a, 210b can be provided on any other suitable embodiment of the interface 50 disclosed herein.

Preferably, the nasal pillows 86 preferably have a bellows structure so as to allow for movement without breaking the seal between the nares and the pillows 86. A central portion of the frame 62 (e.g., between the lower cushions 64a, 64b) can be positioned forward of lateral portions of the frame 62 to provide a space to accommodate the nasal pillows 86 or other nasal elements 82.

The air inlet in the illustrated arrangement is a centrally located elbow 160 that is attached to the supply tube 90 and, preferably, can be swiveled about one axis or two axes (e.g., a ball joint). However, the supply tube 90 can also be a side or horizontal mount, and can be reversible, similar to other embodiments disclosed herein. The elbow 160 can include a bias flow outlet 92.

The attachment location of the headgear 80 can be on the lateral edges of the frame 62 and preferably is positioned between the upper stabilizing pads 114a, 114b and the lower stabilizing pads 64a, 64b in a vertical direction. In some configurations, the attachment location is centrally-located between the upper stabilizing pads 114a, 114b and the lower stabilizing pads 64a, 64b in a vertical direction. This location is advantageous in providing an even distribution of forces between the upper and lower stabilizing pads 114a, 114b, 64a, 64b. The attachment location preferably is close to the face to reduce or minimize rotation of the interface 50 and increase stability. Thus, preferably the headgear 80 is attached to the lateral portions of the frame 62 rather than a central portion in embodiments in which the central portion is spaced outwardly relative to the lateral portions. Moreover, the pads 114a, 114b, 64a, 64b can be low-profile to reduce thickness and/or the spacing of the frame 62 provided by the pads 114a, 114b, 64a, 64b can permit the headgear 80 to be coupled to a rearward surface or face of the frame 62.

The headgear 80 can be of any suitable arrangement, such as any of those described herein. For example, the headgear 80 can be a single or bi-furcated strap and may be stretch or non-stretch. The headgear 80 may include an adjustment mechanism. An adjustable, non-stretch strap may be preferable as it can help to reduce or minimize the likelihood of the nasal pillows 86 to be dislodged from the nares during movement.

Figure 45:
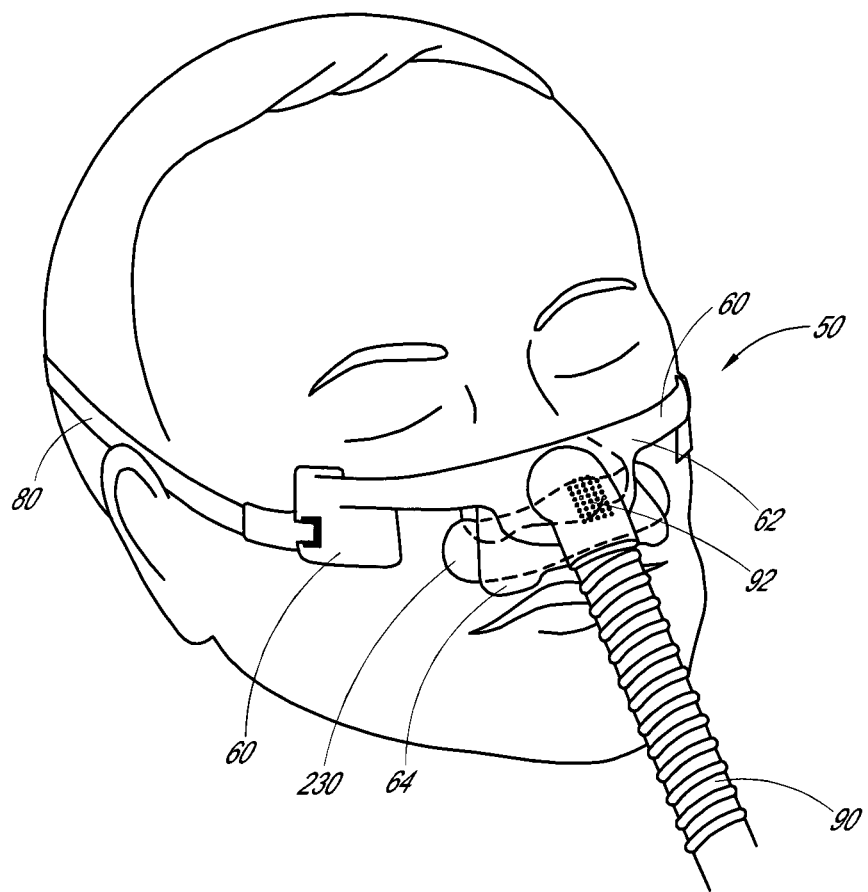
FIG. 45 is a front perspective view of another embodiment of a nasal interface positioned on a user.
Figure 46:
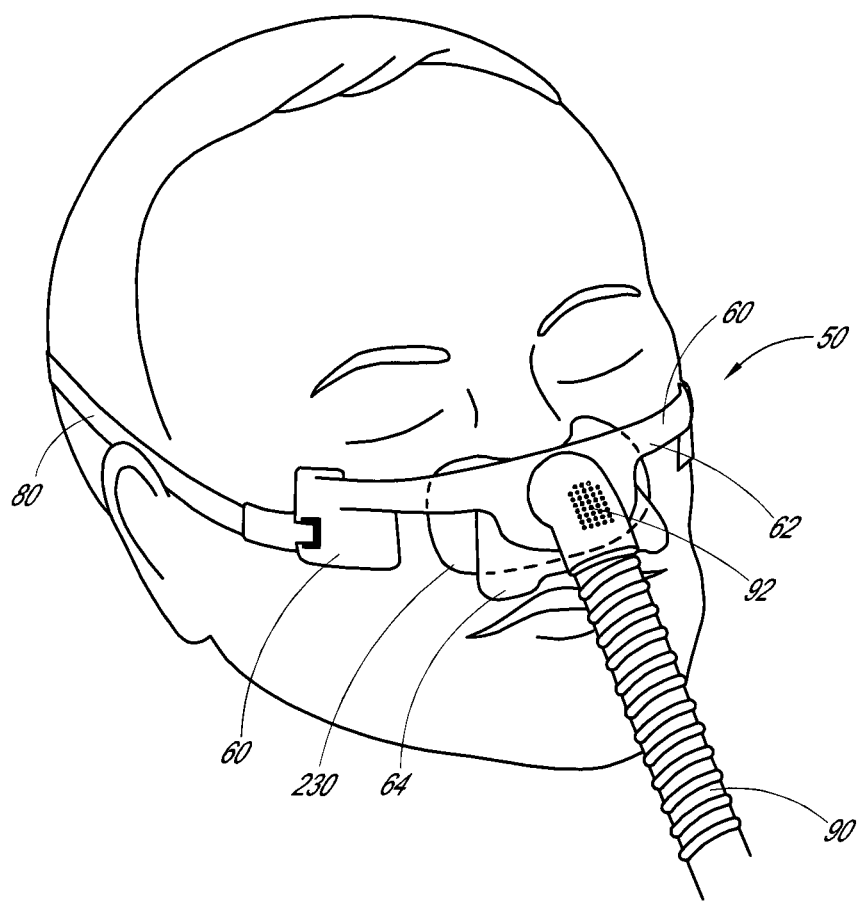
FIG. 46 is a front perspective view of another embodiment of a nasal interface positioned on a user.
Figure 47:
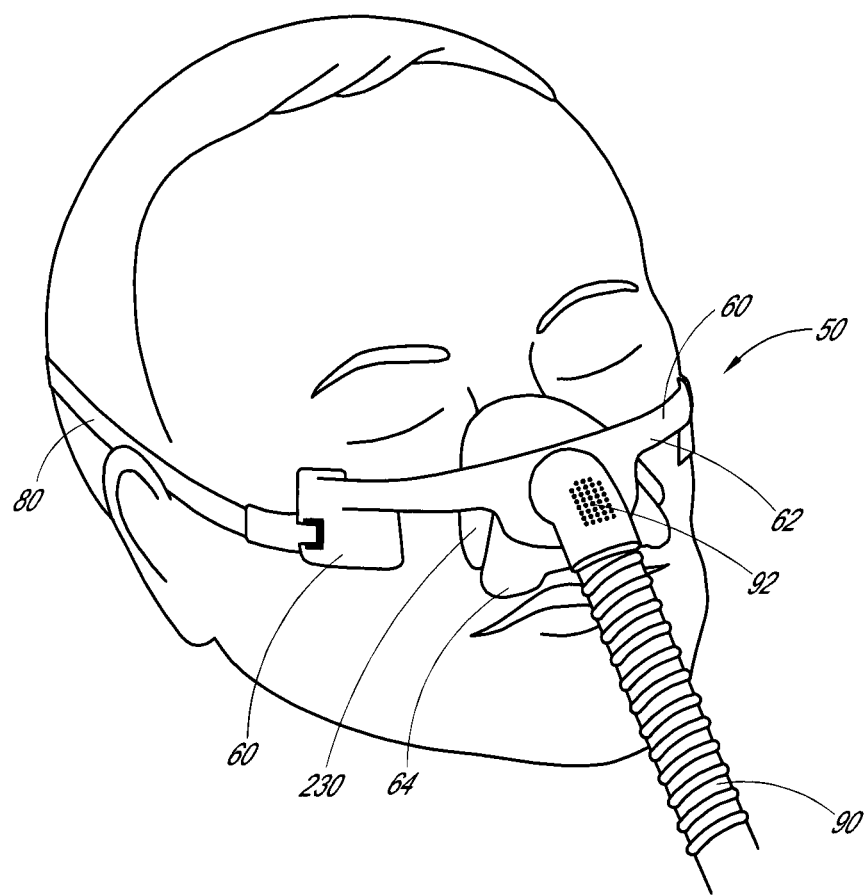
FIG. 47 is a front perspective view of another embodiment of a nasal interface positioned on a user.

FIGS. 45-47 illustrate nasal interfaces 50 similar to the previously-described interfaces. However, each of the nasal interfaces 50 of FIGS. 45-47 includes a nasal interface or nasal delivery element 82 other than the nasal prongs 84 or nasal pillows 86 described in connection with the other nasal interfaces 50 herein. In particular, the interfaces 50 of FIGS. 45-47 include a nasal element or interface that circumscribes the nares of the user's nose and is referred to herein as a nasal seal 230. Although shown in connection with a frame 62 similar to the frame 62 of FIG. 1, the stabilising frame 62 can be similar to any other frame disclosed herein or a frame of any other suitable construction. The nasal seal 230 can take one of the forms shown in and described with respect to FIGS. 45-47 or any other form that may be appropriate. It is preferable that the nasal seal 230 is inflatable (e.g., via the supplied breathing gas) so that it can expand to fit the space between the frame and the user, placing minimal force on the user's nose. However, a more traditional seal 230 that utilises compression forces to create a seal could also be used.

As shown in FIG. 45, the seal 230 can be shaped to sit below the nose creating a seal on the lower surfaces of the nose including the columellar. As shown in FIG. 46, the seal 230 can be configured to seal over the tip of the nose, preferably staying below the nasal bridge. As shown in FIG. 47, the seal 230 can be a more traditional configuration which encapsulates the nose and seals across the bridge of the nose. The air-outlet opening may encircle just the nares or a portion of the entire nose, i.e., the tip and alar flanks. Although illustrated with both the lateral arms 60 and the lip rest 64, other configurations are possible that utilize only one of the arms 60 or lip rest 64, as described in connection with other interfaces 50 herein.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. For example, although shown and described in the context of a nasal delivery elements, certain features, aspects and advantages of the disclosed interfaces could be applied to a delivery element that also encompasses the mouth of the user. Thus, references to nasal delivery elements or nasal interfaces can also refer to interfaces that encompass or deliver breathing gases to the mouth of the user. Such changes and modifications may be made without departing from the spirit and scope of the invention and without diminishing its attendant advantages. It is therefore intended that such changes and modifications be included within the scope of the invention.

What is claimed is:

1. A nasal interface for delivering respiratory therapy to a user, comprising:
   a frame, the frame comprising a pair of supports configured to contact a face of the user below the nose and on either side of the nose in use, each of the pair of supports comprising a face contacting portion and a non-face contacting portion, the frame further comprising at least two lateral supports, the at least two lateral supports being configured to contact the face of the user on or near opposite lateral sides of the nose of the user and support the frame relative to the nose, the at least two lateral supports comprising a formable material configured to hold its shape once deformed to permit a position of the at least two lateral supports to be customized by the user, each of the at least two lateral supports comprising a free end and a lateral face contacting portion at said free end, the lateral face contacting portion configured to contact the face of the user in use;
   at least one nasal delivery element supported by the frame and that is configured to deliver a flow of breathing gas to nares of the user;
   a conduit that is configured to deliver the flow of breathing gas to the at least one nasal delivery element; and
   a headgear that is configured to secure the frame to a head of the user.

2. The nasal interface of claim 1, wherein a retention force of the headgear is translated to the frame and then to the face of the user through the at least two lateral supports.

3. The nasal interface of claim 1, wherein a retention force of the headgear is translated to the at least two lateral supports and then to the face of the user with the frame positioning the at least two lateral supports relative to one another.

4. The nasal interface of claim 1, wherein the at least one nasal delivery element is a pair of nasal delivery elements each comprising a nasal prong.

5. The nasal interface of claim 1, wherein each of the at least two lateral supports are configured to be located on or near a junction of a zygomatic bone and a maxilla of the user.

6. The nasal interface of claim 1, wherein the pair of supports located on the face of the user below the nose and on either side of the nose are configured to be located on or near a maxilla above a lip of the user.

7. The nasal interface of claim 1, wherein at least a central portion of the frame is spaced away from contact with the face of the user.

8. The nasal interface of claim 1, wherein the headgear comprises a front portion that is configured to extend rearwardly from each of a pair of cheeks of the user and a top portion that is configured to extend over a crown of the head of the user, wherein one or both of the front portion and the top portion is constructed from a rigid or semi-rigid material.

9. The nasal interface of claim 1, wherein a position of each of the lateral supports is adjustable.

10. The nasal interface of claim 1, further comprising a pair of stabilizing portions that are configured to be positioned to contact opposite sides of the nose of the user to assist in stabilizing the nasal interface in a lateral direction on the face of the user.

11. The nasal interface of claim 1, wherein the frame comprises a pair of hinged members pivotally coupled to a main portion of the frame, each of the pair of hinged members carrying or defining a respective one of the lateral supports.

12. The nasal interface of claim 1, wherein the application of a force exceeding a deformation threshold of one of the at least two lateral supports plastically deforms the respective lateral support.

13. The nasal interface of claim 1, wherein the pair of supports are removable and/or replaceable.

14. The nasal interface of claim 1, wherein each of the at least two lateral supports comprises a lateral arm, and wherein said free end extends rearwardly from the lateral arm.

15. The nasal interface of claim 1, wherein the at least two lateral supports comprise a first lateral support defining a first lateral arm and a second lateral support defining a second lateral arm.

16. The nasal interface of claim 15, wherein the first and second lateral arms are supported by or integrated with the frame.

17. The nasal interface of claim 15, wherein a length of the first and second lateral arms is adjustable by telescopic movement.

18. The nasal interface of claim 15, wherein the first and second lateral arms are configured to be positioned such that the first and second lateral supports are located on inner cheeks adjacent the nose of the user.

19. The nasal interface of claim 1, wherein the formable material comprises a formable wire.

20. The nasal interface of claim 19, wherein the formable wire is embedded within the at least two lateral supports.

21. The nasal interface of claim 1, wherein each of the pair of supports comprises one of the at least two lateral supports extending from a respective one of the pair of supports.

22. The nasal interface of claim 21, wherein said one of the at least two lateral supports extends from the non-face contacting portion of the respective one of the pair of supports.

* * * * *